United States Patent [19]
Yatvin et al.

[11] Patent Number: 6,024,977
[45] Date of Patent: Feb. 15, 2000

[54] COVALENT POLAR LIPID CONJUGATES WITH NEUROLOGICALLY ACTIVE COMPOUNDS FOR TARGETING

[75] Inventors: Milton B. Yatvin, Portland, Oreg.; Michael H. B. Stowell, Pasadena, Calif.; Michael J. Meredith, Lake Oswego, Oreg.

[73] Assignee: Oregon Health Sciences University, Portland, Oreg.

[21] Appl. No.: 08/923,015

[22] Filed: Sep. 3, 1997

Related U.S. Application Data

[60] Division of application No. 08/735,977, Oct. 25, 1996, Pat. No. 5,827,819, which is a continuation-in-part of application No. 08/685,152, Jul. 23, 1996, which is a continuation of application No. 08/142,771, Oct. 26, 1993, Pat. No. 5,543,389, which is a continuation-in-part of application No. 07/911,209, Jul. 9, 1992, Pat. No. 5,256,641, which is a continuation-in-part of application No. 07/607,982, Nov. 1, 1990, Pat. No. 5,149,794.

[51] Int. Cl.$^7$ .......... A61K 9/127; A61K 38/00; A61K 31/135; A61K 31/54

[52] U.S. Cl. .......... 424/450; 514/2; 514/649; 514/212; 514/222.2; 514/223.5; 514/224.8; 514/227.5

[58] Field of Search .......... 424/450; 514/2, 514/649, 212, 222.2, 223.5, 227.1, 224.8, 211

[56] References Cited

U.S. PATENT DOCUMENTS

| | | | |
|---|---|---|---|
| 4,780,455 | 10/1988 | Liberman et al. | 514/77 |
| 4,793,986 | 12/1988 | Serino et al. | 424/1 |
| 4,847,240 | 7/1989 | Ryser et al. | 514/12 |
| 5,017,566 | 5/1991 | Bodor | 514/58 |
| 5,023,252 | 6/1991 | Hseih | 514/183 |
| 5,024,998 | 6/1991 | Bodor | 514/58 |
| 5,039,794 | 8/1991 | Wier et al. | 530/399 |
| 5,053,394 | 10/1991 | Ellestad et al. | 514/25 |
| 5,112,863 | 5/1992 | Hashimoto et al. | 514/534 |
| 5,124,146 | 6/1992 | Neuwelt | 424/85.8 |
| 5,149,794 | 9/1992 | Yatvin et al. | 530/399 |
| 5,153,179 | 10/1992 | Eibl | 514/34 |
| 5,177,064 | 1/1993 | Bodor | 514/51 |
| 5,254,342 | 10/1993 | Shen et al. | 424/401 |
| 5,258,453 | 11/1993 | Kopecek et al. | 525/54.1 |
| 5,270,312 | 12/1993 | Glase et al. | 514/252 |
| 5,284,876 | 2/1994 | Shashoua et al. | 514/649 |
| 5,389,623 | 2/1995 | Bodor | 514/169 |
| 5,405,834 | 4/1995 | Bundgaard et al. | 514/18 |
| 5,413,996 | 5/1995 | Bodor | 514/169 |
| 5,434,137 | 7/1995 | Black | 514/17 |
| 5,442,043 | 8/1995 | Fukuta et al. | 530/303 |
| 5,466,683 | 11/1995 | Sterling et al. | 514/80 |
| 5,525,727 | 6/1996 | Bodor | 546/39 |
| 5,543,389 | 8/1996 | Yatvin et al. | 514/2 |
| 5,543,390 | 8/1996 | Yatvin et al. | 514/2 |

FOREIGN PATENT DOCUMENTS

| | | |
|---|---|---|
| 077529 | 4/1983 | European Pat. Off. |
| 109484 | 4/1983 | European Pat. Off. |
| 301223 | 12/1983 | European Pat. Off. |
| 203676 | 12/1986 | European Pat. Off. |
| 279887 | 8/1988 | European Pat. Off. |
| 350287 | 1/1990 | European Pat. Off. |
| WO8502342 | 6/1985 | WIPO |
| WO8900166 | 11/1989 | WIPO |
| WO8910348 | 11/1989 | WIPO |
| WO8911299 | 11/1989 | WIPO |
| WO8902909 | 1/1990 | WIPO |
| WO9000555 | 1/1990 | WIPO |
| WO9001002 | 9/1990 | WIPO |
| WO9010448 | 9/1990 | WIPO |
| WO9004087 | 2/1991 | WIPO |
| WO9101750 | 2/1991 | WIPO |
| WO9104014 | 4/1991 | WIPO |
| WO9104745 | 4/1991 | WIPO |
| WO9102691 | 10/1991 | WIPO |
| WO9114438 | 10/1991 | WIPO |
| WO9116024 | 10/1991 | WIPO |
| WO9116024A | 10/1991 | WIPO |
| WO9119726A | 12/1991 | WIPO |
| WO9401131 | 1/1994 | WIPO |
| WO9401138 | 1/1994 | WIPO |
| WO9402178 | 2/1994 | WIPO |
| WO9403424 | 2/1994 | WIPO |
| WO9406450 | 3/1994 | WIPO |
| WO9425616 | 11/1994 | WIPO |
| WO9507092 | 3/1995 | WIPO |
| WO9522963 | 8/1995 | WIPO |
| WO9532002 | 11/1995 | WIPO |
| WO9600537 | 1/1996 | WIPO |
| WO9604001 | 2/1996 | WIPO |
| WO9622303 | 7/1996 | WIPO |

OTHER PUBLICATIONS

Abbas et al., "Antigen Presentation and T Cell Antigen Recognition," *Cellular as J. Mol. Immunol.* (W.B. Saunders Co.; Philadelphia), pp. 116–136 (1988).

(List continued on next page.)

*Primary Examiner*—Theodore J. Criares
*Attorney, Agent, or Firm*—McDonnell Boehnen Hulbert & Berghoff

[57] ABSTRACT

This invention herein describes a method of facilitating the entry of drugs into cells and tissues at physiologically protected sites at pharmicokinetically useful levels and also a method of targeting drugs to specific organelles within the cell. This polar lipid/drug conjugate targeting invention embodies an advance over other drug targeting methods known in the prior art, because the invention provides drug concentrations in such physiologically protected sites that can reach therapeutically-effective levels after administration of systemic levels much lower than are currently administered to achieve a therapeutic dose. This technology is appropriate for use with psychotropic, neurotropic and neurological drugs, agents and compounds, for rapid and efficient introduction of such agents across the blood-brain barrier. Further, the invention provides means for retention and prolonged enzymatic release of psychotropic, neurotropic and neurological drugs, agents and compounds comprising the conjugates of the invention, in the brain and central nervous system.

28 Claims, 12 Drawing Sheets

OTHER PUBLICATIONS

Afzelius et al., *Biochim. Biophys. Acta* 979:231–238 (1989).

Alvarez–Dominquez et al., "Role of Complement Component C1q in Phagocytosis of *Listeria monocytogenes* by Murine Macrophage–Like Cell Lines," *Infect. Immun.* 61:3644–3672 (1993).

Anderson et al., *J. Am. Chem. Soc.* 85: 3039 (1963).

Ashborn et al., Anti–HIV Activity of CD4–Pseudomonas Exotoxin on Infected Primary Human Lymphocytes and Monocyte/Macrophages, *J. Infect. Dis.* 163: 703–709 (1991).

Baer, *Can. J. Biochem. Phys.* 34:288–304 (1955).

Bai and Amidon, "Structural Specificity of Mucosal–Cell Transport and Metabolism of Peptide Drugs: Implications for Oral Peptide Drug Delivery," *Pharm. Res.* 9: 969–978 (1992).

Bai et al., "Utilization of Peptide Carrier System to Improve Intestinal Absorption: Targeting Prolidase as a Prodrug–Converting Enzyme," *J. Pharm. Sci.* 81: 113–116 (1992).

Barlow et al., "Mast cells and T lymphocytes in chronic urticaria," *Clinical & Experimental Allergy* 25: 317–322 (1995).

Baroni et al., "Expression of HIV in Lymph Node Cells of LAS Patients: Immunohistology, In Situ Hybridization, and Identification of Target Cells," *Am. J. Pathol.* 133: 498–506 (1988).

Berdel et al., *Lipids* 22: 943–946 (1987).

Bickel et al., "Pharmacologic effects in vivo in brain by vector–mediated peptide drug delivery," *Proc. Natl. Acad. Sci. USA* 90: 2618–2622 (1993).

Blakey, "Drug Targeting with Monoclonal Antibodies," *Acta Oncol.* 31: 91–97 (1992).

Blight et al., "Detection of hepatitis C virus RNA by in situ hybridization," *Liver* 12: 286–289 (1992).

Blum et al., "Bloood clearance and organ deposition of intravenously administered colloidal particles: the effects of particle size, nature and shape," *Int. J. Pharm.* 12: 135–146 (1982).

Boehnlein et al., "Characterization of Esterase and Alcohol Dehydrogenase Activity in Skin. Metabolism of Retinyl Palmitate to Retinol (Vitamin A) During Percutaneous Absorption," *Pharmaceutical Research* 11: 1155–1159 (1994).

Boman et al., "Cell–free immunity in Cecropia: A model system for antibacterial proteins," *Eur. J. Biochem.* 201: 23–31 (1990).

Borissova et al., "Biodegradable Microspheres. 17. Lysosomal Degradation of Primaquine–Peptide Spacer Arms," *Journal of Pharmaceutical Sciences*, vol. 84, No. 2, Feb. 1995, pp. 256–262.

Bou–Gharios et al., "Expression of ectopeptidases in scleroderma," *Annals of Rheumatic Disease* 54: 111–116 (1995).

Brewster et al., "Improved Delivery through Biological Membranes XXXI: Solubilization and Stabilization of an Estradiol Chemical Delivery System by Modified β–Cyclodextrins," *J. Pharm. Sci.* 77: 981–985 (1985).

Bromberg et al., "Detection of *Borditella pertussis* Associated with the Alveolar Macrophages of Children with Human Immunodeficiency Virus Infection," *Infect. Immun.* 59: 4715–4719 (1991).

Brown & Silvius, *Biochim. Biophys. Acta* 1023: 341–351 (1990).

Brown et al., "Induction of Cell Surface Peptidase Activity: A Global Response to Cell Stress Correlated with Apoptosis," *J. Cellular Biochemistry* 54: 320–331 (1994).

Brynestad et al., *J. Virol.* 64:680–685 (1990).

Buchmeier and Heffron, "Induction of Salmonella Stress Proteins upon Infection of Macrophages," *Science* 248: 730–732 (1990).

Büyüktimkin et al., "Synthesis and Enhancing Effect of Dodecyl 2–(N,N–Dimethylamino)propionate on the Transepidermal Delivery of Indomethacin, Clondine, and Hydrocotisone," *Pharmaceutical Research* 10: 1632–1637 (1993).

Chang, "*Leishmania donovani*: Promastigote–Macrophage Surface Interactions in Vitro," *Exp. Parisitol.* 48:175–189 (1979).

Clarke et al., "Detection of HIV–1 in human lung macrophages using the polymerase chaine reaction," *AIDS* 4: 1133–1136 (1990).

Comiskey & Health, *Biochim, Biophys. Acta* 1024: 307–317 (1990).

Cordier et al., "In vivo Activation of Alveolar Macrophages in Ovine Lentivirus Infection," *Clin. Immunol. Immunopathol.* 55: 355–367 (1990).

Couveur and Puisieux, "Nano–and microparticles for the delivery of polypeptides and proteins," *Adv. Drug Deliv. Rev.* 10: 141–162 (1993).

Dachun et al., "Localization and Quantification of the Nonspecific Esterase in Injured Skin for Timing of Wounds," *Forensic Science International* 53: 202–213 (1992).

De Magistris et al., "Antigen Analog–Major Histocompatibility Complexes Act As Antagonists of the T Cell Receptor," *Cell* 68: 625–634 (1992).

Debs et al., *Biochim. Biophys. Acta* 901: 183–190 (1987).

Deres et al., *Nature* 342:561–564 (1989).

Dreyer et al., *Proc. Natl. Acad. Sci. USA* 86: 9752–9756 (1989).

Duncan, "Drug–polymer conjugates: potential for improved chemotherapy," *Anticancer Drugs* 3: 175–210 (1992).

Elliott et al., "Naturally processed peptides," *Nature* 348: 195–197 (1990).

Embretson et al., "Massive convert infection of helper T lymphocytes and macrophages by HIV during the incubation period of AIDS," *Nature* 362: 359–361 (1993).

Falk et al., "Allele–specific motifs revealed by sequencing of self–peptides eluted from MHC molecules," *Nature* 351: 290–291 (1991).

Falk et al., "Cellular peptide composition governed by major histocompatability complex class I molecules," *Nature* 348: 248–251 (1990).

Faulk et al., "Transferrin–Adriamycin Conjugates which Inhibit Tumor Cell Proliferation without Interaction with DNA Inhibit Plasma Membrane Oxidoreductase and Proton Release in K562 Cells," *Biochem. Int.* 25: 815–822 (1991).

Faustman et al., "Linkage of Faulty Major Histocompatability Complex Class I to Autoimmune Diabetes," *Science* 254: 1756–1776 (1991).

Franssen et al., "Low Molecular Weight Proteins as Carrier for Renal Drug Targeting: Preparation of Drug–Protein Conjugates and Drug–Spacer Derivatives and Their Catabolism in Renal Cortex Homogenates and Lysosomal Lysates," *J. Med. Chem.* 35: 1246–1259 (1992).

Frehel et al., "Intramacrophage Growth of *Mycobacterium avium* during Infection of Mice," *Infect. Immun.* 59: 2207–2214 (1991).

Friedman et al., "Uptake and Intracellular Survival of *Bordatella pertussis* in Human Macrophages," *Infect. Immun.* 60: 4578–4585 (1992).

Frisch et al., "Parameters affecting the immunogenicity of a liposome–associated synthetic hexapeptide antigen," *Eur. J. Immun.* 21: 185–193 (1991).

Gaspar et al., "Drug targeting with polyalkylcyanoacrylate nanoparticles: in vitro activity of primaquine–loaded nanoparticles against intracellular *Leishmania donovani*," *Ann. Trop. Med. Parasitol.* 86: 41–49 (1992).

Gendelman et al., "Slow, persistent replication of lentiviruses: Role of tissue macrophages and endoplasmic reticulum antigen binding," *Nature* 353: 134–139 (1991).

German & Hendrix, "MHC class II structure, occupancy and surface expression determined by postendoplasmic reticulum antigen binding," *Nature* 353: 134–139 (1991).

Groisman et al., "Resistance to host antimicrobial peptides is necessary for Salmonella virulence," *Proc. Natl. Acad. Sci. USA* 89: 11939–11943 (1992).

Guéry et al., Selective Immunosuppression by Administration of Major Histocompatability Complex (MHC) Class II–binding Peptides. I. Evidence for In Vivo MHC Blockade Preventing T Cell Activation, *J. Exp. Med.* 175: 1345–1352 (1992).

Halstead et al., "Dengue Viruses and Mononuclear Phagocytes: I. Infection Enhancement by Non–Neutralizing Antibody," *J. Exp. Med.* 146: 201–217 (1977).

Hashimoto et al., *Biochim. Biophys. Acta* 816: 163–168 (1985).

Hashimoto et al., *Biochim. Biophys. Acta* 816: 169–178 (1985).

Heath and Martin, *Chem. Phys. Lipids* 40: 347–358 (1986).

Heath et al., *Biochim.Biophys. Acta* 862: 72–80 (1986).

Heath, *Methods in Enzymol.* 149: 111–119 (1980).

Heinrich et al., "In–vivo Release of a GnRH Agonist from a Slow–release Poly(lactide–glycolide) Copolymer Preparation: Comparison in Rat, Rabbit and Guinea–Pig," *J. Pharm. Pharmacol.* 43: 762–765 (1991).

Henrikus and Kampffmeyer, "Ester hydrolysis conjugation reactions in intact skin and skin homogenate, and by liver esterase of rabbits," *Xenobiotica* 22: 1357–1366 (1992).

Heymann et al., "Organophosphate Sensitive and Insensitive Carboxylesterases in Human Skin," *Chem. Biol. Interactions* 87: 217–226 (1993).

Hopp, "Immunogenicity of a Synthetic HBsAg Peptide: Enhancement by Conjugation to a Fatty Acid Carrier," *Mol. Immunol.* 21: 13–16 (1984).

Horwitz and Maxfield, "*Legionella pneumphila* Inhibits Acidification of its Phagosome in Human Monocytes," *J. Cell Biol.* 99: 1936–1943 (1984).

Horwitz, "Interactions between Macrophages and *Legionella pneumophila*," *Curr. Top. Microbiol. Immunol.* 181:265–282 (1992).

Horwitz, "The Legionnaires' Disease Bacterium (*Legionella pneumophila*) Inhibits Phagosome–Lysosome Function in Human Monocytes," *J. Exp. Med.* 158: 2108–2126 (1983).

Hostetler et al., *J. Biol. Chem.* 265: 6112–6117 (1990).

Hunter et al., "Vesicular Systems (Niosomes and Liposomes) for Delivery of Sodium Stibogluconate in Experimental Murine Visceral Leishmaniasis," *J. Pharm. Pharmacol.* 40: 161–165 (1988).

Jacobson et al., *FEBS Lett.* 225: 97–102 (1987).

Jardetzky et al., "Identification of self peptides bound to purified HLA–B27," *Nature* 353: 326–329 (1991).

Jones and Hirsch, "The Interaction between *Toxoplasma gondii* and Mammalian Cells," *J. Exp. Med.* 136:1173–1194 (1972).

Kanno et al., "Aleutian Mink Disease Parvovirus Infection of Mink Peritoneal Macrophages and Human Macrophage Cell Lines," *J. Virol.* 67:2075–2082 (1985).

Kanno et al., "Identification of Aleutian Mink Disease Parvovirus Transcripts in Macrophages of Infected Adult Mink," *J. Virol.* 66:5305–5312 (1992).

King et al., "In Vivo Selection of Lymphocyte–Tropic and Macrophage–Tropic Variants of Lymphocytic Chorimeningitis Virus during Persistent Infection," *J. Virol.* 64: 5611–5616 (1990).

Kinsky & Loeder, *Biochim. Biophys. Acta* 921: 96–103 (1987).

Kinsky et al., *Biochim. Biophys. Acta* 885: 129–135 (1986).

Kinsky et al., *Biochim. Biophys. Acta* 917: 211–218 (1987).

Kishimoto, *Chem. Phys. Lipids* 15: 33–36 (1975).

Koenig et al., "Detection of AIDS Virus in Macrophages in Brain Tissue from AIDS Patients with Encephalopathy," *Science* 233: 1089–1093 (1986).

Kondo et al., "Latent human herpesvirus 6 infection of human monocytes/macrophages," *J. Gen. Virol.* 72: 1401–1408 (1991).

Koval & Pagano, "Lipid Recycling between the Plasma Membrane and Intracellular Compartments: Transport and Metabolism of Fluorescent Sphingomyelin Analogues in Cultured Fibroblasts," *J. Cell Biol.* 108: 2169–2181 (1989).

Kratz et al., "Keratinocyte conditioned medium stimulates type IV collagenase synthesis in cultured human keratinocytes and fibroblasts," *Brit. J. Dermatology* 133: 842–846 (1995).

Kreeger, *The Scientist*, Sep. 16, 1996, p. 6.

Krowka et al., *J. Immunol.* 144: 2535–2540 (1990).

Kubota et al., "Metabolism and Degradation of Betamethasone 17–Valerate in Homogenized Living Skin Equivalent," *Dermatology* 188: 13–17 (1994).

Kung and Redemann, *Biochim. Biophys. Acta* 862: 435–439 (1986).

Lamont et al., "The use of Peptide Analogs with Improved Stability and MHC Binding Capacity to Inhibit Antigen Presentation In Vitro and In Vivo," *J. Immunol.* 144: 2493–2498 (1990).

Lanzavecchia et al., "Irreversible association of peptides with class II MHC molecules in living cells," *Nature* 357: 249–252 (1992).

Larsen et al., "Stability of ketoprofen–dextran ester prodrugs in homogenates of various segments of the pig GI tract," *Acta Pharm. Nord.* 3: 41–44 (1991).

Lee et al., "Antibacterial peptides from pig intestines: Isolation of a mammalian cecropin," *Proc. Natl. Acad. Sci. USA* 86: 9159–9162 (1989).

Lehninger, *Biochemistry*, 2d ed., Chapters 11 & 24, Worth Publishers: New York, 1975.

Lehrer et al., "Defensins: Endogenous Antibiotic Peptides of Animal Cells," *Cell* 64: 229–230 (1991).

Lin et al., "Preparation of Enteric–Coated Microspheres of myplasma hyopneumoniae vaccine with cellulose acetate; (ii) effect of temperature and ph on the stability and release behaviour of microspheres," *Journal of Microencapsulation*, vol. 8, No. 4: 537–545 (1991).

Lipozencic et al., "Langerhans cells in the immunopathology of contact allergic dermatitis," *Eur. J. Histochem* 38: 303–310 (1994).

Loughery et al., *J. Immunol. Methods* 132: 25–35 (1990).

MacDonald, *J. Biol. Chem.* 265: 13533–13539 (1990).
Maciejewski et al., "Infection of Mononucleated Phagocytes with Human Cytomegalovirus," *Virol.* 195: 327–336 (1993).
Matsura et al., *J. Chem. Soc. Chem. Comm. xx:* 451–459 (1976).
Mauel, "Quantitative Release of Live Micro–organism from Infected Macrophages by Sodium Dodecyl Sulfate," *Nature New Biol.* 244:93–94 (1973).
Mauel, "Macrophage–Parasite Interactions in Leishmania Infections," *J. Leukocyte Biol.* 47: 187–193 (1990).
McEntee et al., "Rhesus monkey macrophages infected with simian immunodeficiency virus cause rapid lysis of CD4–bearing lymphocytes," *J. Gen. Virol.* 72: 317–324 (1991).
Meltzer and Gendelman, "Mononuclear Phagocytes as Targets, Tissue Reservoirs, and Immunoregulatory Cells in Human Immunodeficiency Virus Disease," *Curr. Topics Microbiol. Immunol.* 181: 239–263 (1992).
Menger et al., "Synthesis of a Lipid/Peptide/Drug Conjugate: N4–(Acylpeptidyl)–ARA–C," *Bioconjugate Chemistry* 5: 162–166 (1994).
Moehrle et al., "Aminopeptidase M and dipeptidyl peptidase IV activity in epithelial skin tumors: a histochemical study," *J. Cutaneous Pathology* 22: 241–247 (1995).
Mukhergee & Heidelberger, *Cancer Res.* 22: 815–822 (1962).
Murray et al., "Experimental Visceral Leishmaniasis: Production of Interleukin 2 and Interferon y, Tissue Immune Reaction, and Response to Treatment with Interleukin 2 and Interferon y," *J. Immunol.* 138: 2290–2296 (1987).
Narayan et al., "Lentivirus Induced Arthritis in Animals," *J. Rheumatol.* 32:25–32 (1992).
Negre et al., "Antileishmanial Drug Targeting through Glycosylated Polymers Specifically Internalized by Macrophage Membrane Lectins," *Antimicrob. Agents and Chemother.* 36: 2228–2232 (1992).
Neto et al., *Biochem. Biophys. Res. Commun.* 171: 458–464 (1990).
Neurath et al., *J. Gen. Virol.* 65;1009–1014 (1984).
Ng & Heath, *Biochim. Biophys. Acta* 981: 261–268 (1989).
Nogueira and Cohn, "*Trypanosoma cruzi:* Mechanisms of Entry and Intracellular Fate in Mammalian Cells," *J. Exp. Med.* 143:1402–1420 (1976).
Nothnagel, *Biochim. Biophys. Acta* 980: 209–219 (1989).
Pagano et al., *J. Biol. Chem.* 258: 2034–2040 (1983).
Panuska et al., "Productive Infection of Isolated Human Alveolar Macrophages by Respiratory Syncytial Virus," *J. Clin. Invest.* 86: 113–119 (1990).
Pardridge, "Opioid Peptide Drug Development: Transport of Opioid Chimeric Peptides through the Blood–Brain Barrier," *NIDA Res. Monograph* 120: 153–168 (1992).
Parham, "Transporters of delight," *Nature* 348: 674–675 (1990).
Paul and Anderson, *J. Am. Chem. Soc.* 82: 4596–4600 (1960).
Payne et al., "Phagocytosis of *Legionella pneumophila* is Mediated by Human Monocyte Complement Receptors," *J. Exp. Med.* 166: 1377–1389 (1987).
Rahman et al., *Life Sci.* 31: 2061–2071 (1982).
Remy et al., *J. Org. Chem.* 27: 2491–2500 (1962).
Rosenberg et al., *J. Neurochem.* 48: 865–875 (1987).
Rowlinson–Busza and Epenetos, "Targeted delivery of biologic and other antineoplastic agents," *Curr. Opin. Oncol.* 4: 1142–1148 (1992).

Rubinstein et al., "In Vitro Evaluation of Calcium Pectinate: A Potential Colon–Specific Drug Delivery Carrier," *Pharm. Res.* 10: 258–263 (1993).
Sadegh–Nasseri and Germain, "A role for peptide in determining MCH class II structure," *Nature* 353: 167–170 (1991).
Saffran et al., "A New Approach to the Oral Administration of Insulin and Other Peptide Drugs," *Science* 233: 1081–1084 (1986).
Salord et al., *Biochim. Biophys. Acta* 886: 64–75 (1986).
Schlessinger and Horwitz, "Phagocytosis of Leprosy Bacilli is Mediated by Complement Receptors CR1 and CR3 on Human Monocytes and Complement Component C3 in Serum," *J. Clin. Invest.* 85: 1304–1314 (1990).
Schmitt et al., "Multiplication of Human Immunodeficiency Virus in Primary Cultures of Human Kupffer Cells—Possible Role of Liver Macrophage Infection in the Physiopathology of AIDS," *Res. Virol.* 141: 143–152 (1990).
Schnorr et al., "MxA–Dependent Inhibition of Measles Virus Glycoprotein Synthesis in a Stably Transfected Human Monocytic Cell Line," *J. Virol.* 67: 4760–4768 (1993).
Seifert et al., *Biochem. J.* 267:795–802 (1990).
Sellon et al., "Wild–Type Equine Infectious Anemia Virus Replicates in Vivo Predominantly in Tissue Macrophages, Not in Peripheral Blood Monocytes," *J. Virol.* 66: 5906–5913 (1992).
Senter et al., "Activation of Prodrugs by Antibody–Enzyme Conjugates," in *Immunobiology of Peptides and Proteins,* vol. VI, pp. 97–105 (1991).
Shanley and Pesanti, "Murine Peritoneal Macrophages Support Murine Cytomegalovirus Replication," *Infect. Immunol.* 41: 1352–1359 (1983).
Shen et al., "Cis–Aconityl Spacer between Daunomycin and Macromolecular Carriers: A Model of pH Sensitive Linkage Releasing Drug from a Lysomotropic Conjugate," *Biochem. Biopys. Res. Commun.* 102:1048–1052 (1981).
Sierra–Honigman et al., "Borna disease virus in peripheral blood mononuclear and bone marrow cells of neonatally and chronically infected rats," *J. Neuroimmunol.* 45: 31–36 (1993).
Sintov et al., "Enzymatic cleavage of disaccharaide side groups in insoluble synthetic polymers: a new method for specific delivery of drugs to the colon," *Biomaterials* 14: 483–490 (1993).
SivaSai et al., "Effect of Recombinant Interferon Gamma Administration on Lesional Monocytes/Macrophages in Lepromatous Leprosy Patients," *Int. J. Leprosy & Other Mycobacterial Diseases* 61: 259–269 (1993).
Small, "From alkanes to phospholipids," *Handbook of Lipid Research: Physical Chemistry of Lipids,* vol. 4, Chapters 4 and 12, Plenum Press, New York, 1986.
Smith and Khorana, *J. Amer. Chem. Soc.* 80: 1141–1145 (1958).
Steim et al., *Biochem. Biophys. Res. Commun.* 171: 451–457 (1990).
Strellrecht–Broomhall, "Evidence for Immune–Mediated Destruction as Mechanism for LCMV–Induced Anemia in Persistently Infected Mice," *Virol. Immunol.* 4: 269–280 (1991).
Strugill–Koszycki et al., "Lack of Acidification in Mycobacterium Phagosomes Produced by Exclusion of the Vesicular Proton–ATPase," *Science* 263: 678–681 (1994).

Trouet et al., "A covalent linkage between danuorubicin and proteins that is stable in serum and reversable by lysosomal hydrolases, as required for a lysomotropic drug–carrier conjugate: In vitro and in vivo studies," *Proc. Natl. Acad. Sci. USA* 79:626–629 (1982).

van Wijk et al., *Biochim. Biophys. Acta* 1084: 307–310 (1991).

Vandenbark et al., *Nature* 341:841–844 (1989).

Verbloom et al., *Synthesis* 1032: 807–809 (1981).

Wada et al., "Salt Formation of Lactic Acid Oligomers as Matrix for Sustained Release of Drugs," *J. Pharm. Pharmacol.* 43: 605–608 (1991).

Wiesúller et al., "The antibody response in BALB/c mice to the *Plasmodium falciparum* circumsporozoite repetitive epitope covalently coupled to syntehtic lipopeptide adjuvant," *Immun.* 72: 109–113 (1991).

Wyrick and Brownridge, "Growth of *Chlamydia psittaci* in Macrophages," *Infect. Immunol.* 19:1054–1060 (1978).

Yatvin et al., "Targeting Lipophilic Prodrugs to Brain, Lung, and Spleen," *Journal of Cellular Biochemistry,* vol. 0, No. 19A: 173 (1995).

Yatvin, "A Multi–Modality Approach for the Treatment of AIDS," *Select. Cancer. Therapeut.* 7: 23–28 (1991).

Zasloff, "Magainins, a class of antimicrobial peptides from *Xenopus skin*:Isolation, characterization of two active forms, and partial cDNA sequence of a precursor," 84:5449–5453 (1987).

Zhang and McCormick, "Uptake of N–(4'–pyridoxyl)amines and release of amines by renal cells: A model transport–enhanced delivery of bioactive compounds," *Proc. Natl. Acad. Sci. USA* 88: 10407–10410 (1991).

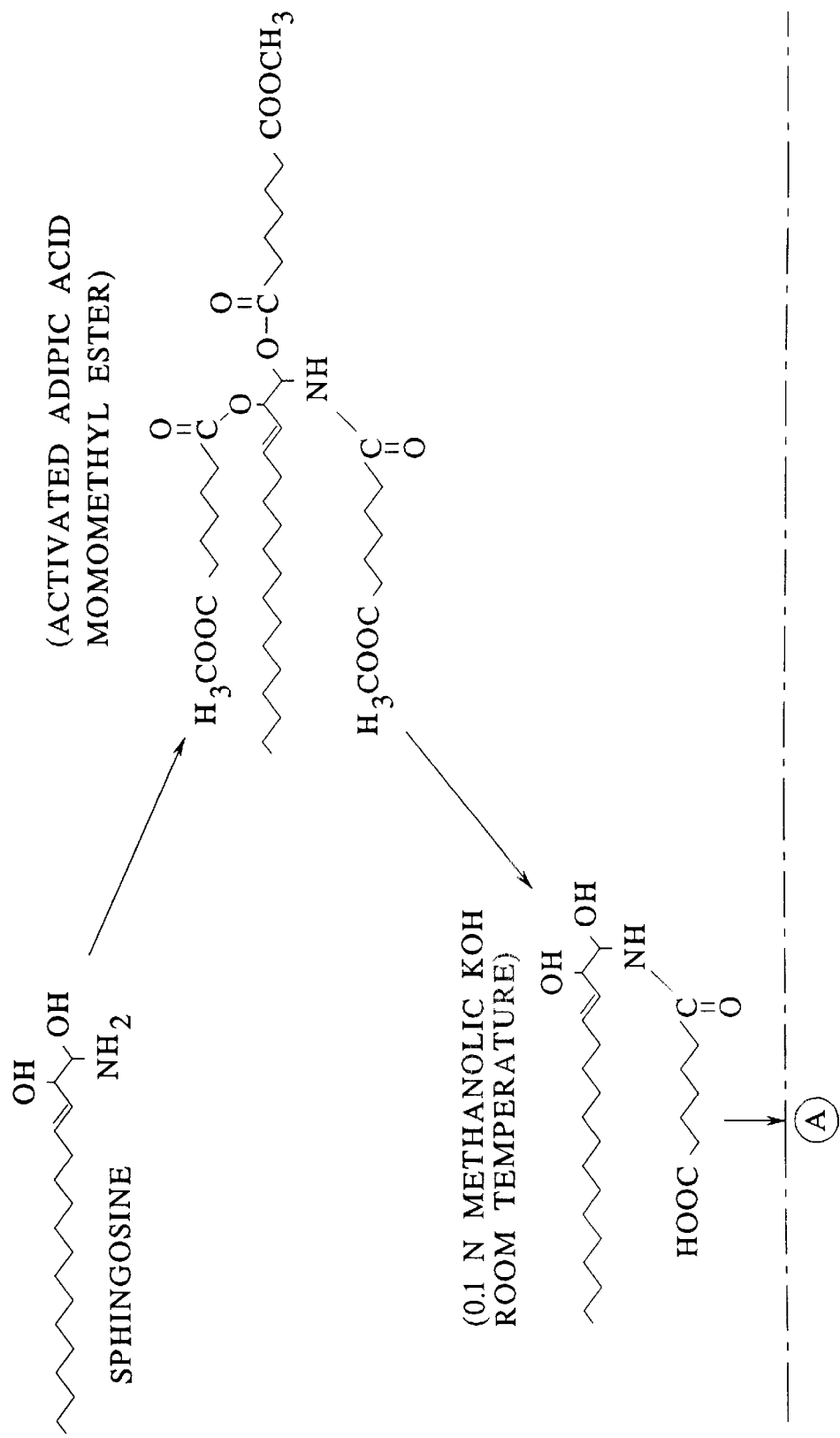

COVALENT POLAR LIPID CONJUGATES WITH NEUROLOGICALLY ACTIVE COMPOUNDS FOR TARGETING

This application is a divisional of application Ser. No. 08/735,977, filed Oct. 25, 1996, now U.S. Pat. No. 5,827,819 which is a continuation-in part of U.S. patent application, Ser. No. 08/685,152, filed Jul. 23, 1996, pending which is also a continuation of U.S. Ser. No. 08/142,771, filed Oct. 26, 1993, now U.S. Pat. 5,543,389, issued Aug. 6, 1992, which is a continuation in part of U.S. Ser. No. 07/911,209 filed July 9, 1992 now U.S. Pat. No. 5,256,641, issued Oct. 26, 1993, which is a continuation-in-part of U.S. patent application Ser. No. 07/607,982, filed Nov. 1, 1990, now U.S. Pat. No. 5,149,794, issued Sep. 22, 1992, each of which are herein incorporated by reference.

This application is also related to U.S. patent application Ser. No. 08/691,891, filed Aug. 1, 1996, now U.S. Pat. No. 5,840,674, issued Nov. 24, 1998, which is a continuation of U.S. Ser. No. 08/441,770, filed May 16, 1995, now U.S. Pat. No. 5,543,391, issued Aug. 6, 1996, and U.S. Pat. No. Ser. No. 08/246,941, filed May 19, 1994, now U.S. Pat. No. 5,543,390, issued Aug. 6, 1996.

BACKGROUND OF THE INVENTION

1. Field of the Invention

A major goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. One common example of the need for such specificity is in the field of neurologic agent therapy for the treatment of diseases of the central nervous system, particularly the brain, which is protected by a layer of endothelial cells and other structures collectively known as the blood-brain barrier. In the pharmacological and neurologic arts, it is well-recognized that the inability to deliver effective amounts of neurotropic, psychotropic and anticonvulsant drugs and agents across the blood-brain barrier severely limits the therapeutic efficacy of such pharmaceutical compounds and can prevent treatment of neurologic disease. In addition, the use of even effective neurologic agents is further limited by systemic toxicity resulting from the high systemic concentrations that must be administered to achieve a therapeutic concentration of such agents in the brain, central nervous system and other neurological structures. Similar considerations apply in other organs and tissues in mammals that are protected by such blood-related barriers, such as the testes.

In addition, it is recognized in the medical arts that certain subcellular organelles are the sites of pharmacological action of certain drugs or are involved in the biological response to certain stimuli. Specific delivery of diagnostic or therapeutic compounds to such intracellular organelles is thus desirable to increase the specificity and effectiveness of such clinical diagnostic or therapeutic techniques.

Drug Targeting

It is desirable to increase the efficiency and specificity of administration of a therapeutic agent to the cells of the relevant tissues protected by physiological barriers (i.e., such as the blood-brain barrier) in a variety of pathological states. This is particularly important as relates to psychotropic, neurological and neurotropic agents. Such agents typically have systemic effects, including renal and hepatotoxicity, hematopoietic suppression, teratogenic capacity, partitioning into breast milk and other pleiotropic cytotoxic effects that damage or otherwise deleteriously impact on uninvolved cells and tissues. This is particularly the case in delivering psychotropic, neurotropic and neurological agents to physiologically protected sites, since high systemic concentrations of such agents are required to promote partitioning of a sufficient amount of the psychotropic, neurotropic and neurological agents into the protected sites to achieve a therapeutic result. Thus, an efficient delivery system which would enable the delivery of such drugs specifically to cells and tissues in such physiologically protected sites would increase the efficacy of treatment and reduce the associated "side effects" of such drug treatments, and also serve to reduce morbidity and mortality associated with clinical administration of such drugs.

Numerous methods for enhancing the biological activity and the specificity of drug action have been proposed or attempted (see, for example, Kreeger, 1996, *The Scientist*, Sep. 16, 1996, p. 6). To date, however, efficient or specific drug delivery remains to be predictably achieved.

U.S. Pat. No. 5,017,566, issued May 21, 1991 to Bodor disclose β- and γ-cyclodextrin derivatives comprising inclusion complexes of lipoidal forms of dihydropyridine redox targeting moieties.

U.S. Pat. No. 5,023,252, issued Jun. 11, 1991 to Hseih disclose the use of pharmaceutical compositions comprising a neurologically active drug and a compound for facilitating transport of said drug across the blood-brain barrier including a macrocyclic ester, diester, amide, diamide, amidine, diamidine, thioester, dithioester, thioamide, ketone or lactone.

U.S. Pat. No. 5,024,998, issued Jun. 18, 1991 to Bodor disclose parenteral solutions of aqueous-insoluble drugs with β- and γ-cyclodextrin derivatives.

U.S. Pat. No. 5,039,794, issued Aug. 13, 1991 to Wier et al. disclose the use of a metastatic tumor-derived egress factor for facilitating the transport of compounds across the blood-brain barrier.

U.S. Pat. No. 5,112,863, issued May 12, 1992 to Hashimoto et al. disclose the use of N-acyl amino acid derivatives as antipsychotic drugs for delivery across the blood-brain barrier.

U.S. Pat. No. 5,124,146, issued Jun. 23, 1992 to Neuwelt disclose a method for delivery of therapeutic agents across the blood-brain barrier at sites of increase permeability associated with brain lesions.

U.S. Pat. No. 5,153,179, issued Oct. 6, 1992 to Eibl disclose acylated glycerol and derivatives for use in a medicament for improved penetration of cell membranes.

U.S. Pat. No. 5,177,064, issued Jan. 5, 1993 to Bodor disclose the use of lipoidal phosphonate derivatives of nucleoside antiviral agents for delivery across the blood-brain barrier.

U.S. Pat. No. 5,254,342, issued Oct. 19, 1993 to Shen et al. disclose receptor-mediated transcytosis of the blood-brain barrier using the transferrin receptor in combination with pharmaceutical compounds that enhance or accelerate this process.

U.S. Pat. No. 5,258,402, issued Nov. 2, 1993 to Maryanoff disclose treatment of epilepsy with imidate derivatives of anticonvulsive sulfamate.

U.S. Pat. No. 5,270,312, issued Dec. 14, 1993 to Glase et al. disclose substituted piperazines as central nervous system agents.

U.S. Pat. No. 5,284,876, issued Feb. 8, 1994 to Shashoua et al., disclose fatty acid conjugates of dopanergic drugs for tardive dyskinesia.

U.S. Pat. No. 5,389,623, issued Feb. 14, 1995 to Bodor disclose the use of lipoidal dihydropyridine derivatives of anti-inflammatory steroids or steroid sex hormones for delivery across the blood-brain barrier.

U.S. Pat. No. 5,405,834, issued Apr. 11, 1995 to Bundgaard et al. disclose prodrug derivatives of thyrotropin releasing hormone.

U.S. Pat. No. 5,413,996, issued May 9, 1995 to Bodor disclose acyloxyalkyl phosphonate conjugates of neurologically-active drugs for anionic sequestration of such drugs in brain tissue.

U.S. Pat. No. 5,434,137, issued Jul. 18, 1995 to Black disclose methods for the selective opening of abnormal brain tissue capillaries using bradykinin infused into the carotid artery.

U.S. Pat. No. 5,442,043, issued Aug. 15, 1995 to Fukuta et al. disclose a peptide conjugate between a peptide having a biological activity and incapable of crossing the bloodbrain barrier and a peptide which exhibits no biological activity and is capable of passing the blood-brain barrier by receptor-mediated endocytosis.

U.S. Pat. No. 5,466,683, issued Nov. 14, 1995 to Sterling et al. disclose water soluble analogues of the anticonvulsant Tegretol ® (carbamazepine) for the treatment of epilepsy.

U.S. Pat. No. 5,525,727, issued Jun. 11, 1996 to Bodor disclose compositions for differential uptake and retention in brain tissue comprising a conjugate of a narcotic analgesic and agonists and antagonists thereof with a lipoidal form of dihydropyridine that forms a redox salt upon uptake across the blood-brain barrier that prevents partitioning back to the systemic circulation thereafter.

International Pat. Application Publication Number WO85/02342, published Jun. 6, 1985 for Max-Planck Institute disclose a drug composition comprising a glycerolipid or derivative thereof.

International Patent Application Publication Number WO089/11299, published Nov. 30, 1989 for State of Oregon disclose a chemical conjugate of an antibody with a an enzyme which is delivered specifically to a brain lesion site for activating a separately-administered neurologicallyactive prodrug.

International Patent Application Publication Number WO91/04014, published Apr. 4, 1991 for Synergen, Inc. disclose methods for delivering therapeutic and diagnostic agents across the blood-brain barrier by encapsulating said drugs in liposomes targeted to brain tissue using transportspecific receptor ligands or antibodies.

International Patent Application Publication Number WO91/04745, published Apr. 18, 1991 for Athena Neurosciences, Inc. disclose transport across the blood-brain barrier using cell adhesion molecules and fragments thereof to increase the permeability of tight junctions in vascular endothelium.

International Patent Application Publication Number WO91/14438, published Oct. 3, 1991 for Columbia University disclose the use of a modified, chimeric monoclonal antibody for facilitating transport of substances across the blood-brain barrier.

International Pat. Application Publication Number WO94/01131, published Jan. 20, 1994 for Eukarion, Inc. disclose lipidized proteins, including antibodies.

International Pat. Application Publication Number WO94/03424, published Feb. 17, 1994 for Ishikira et al. disclose the use of amino acid derivatives as drug conjugates for facilitating transport across the blood-brain barrier.

International Patent Application Publication Number WO94/06450, published Mar. 31, 1994 for the University of Florida disclose conjugates of neurologically-active drugs with a dihydropyridine-type redox targeting moiety and comprising an amino acid linkage and an aliphatic residue.

International Patent Application Publication Number WO94/02178, published Feb. 3, 1994 for the U.S. Government, Department of Health and Human Services disclose antibody-targeted liposomes for delivery across the blood-brain barrier.

International Patent Application Publication Number WO95/07092, published Mar. 16, 1995 for the University of Medicine and Dentistry of New Jersey disclose the use of drug-growth factor conjugates for delivering drugs across the blood-brain barrier.

International Patent Application Publication Number WO96/00537, published Jan. 11, 1996 for Southern Research Institute disclose polymeric microspheres as injectable drug-delivery vehicles for delivering bioactive agents to sites within the central nervous system.

International Patent Application Publication Number WO96/04001, published Feb. 15, 1996 for Molecular/ Structural Biotechnologies, Inc. disclose omega-3-fatty acid conjugates of neurologically-active drugs for brain tissue delivery.

International Patent Application Publication Number WO96/22303, published Jul. 25, 1996 for the Commonwealth Scientific and Industrial Research Organization disclose fatty acid and glycerolipid conjugates of neurologically-active drugs for brain tissue delivery.

An additional challenge in designing an appropriate drug delivery scheme is to include within the drug conjugate a functionality which could either accelerate or reduce the rate at which the drug is released upon arrival at the desired site. Such a functionality would be especially valuable if it allowed differential rates of drug release, or specific release only at the appropriate drug target site.

There remains a need in the art for an effective means for the specific delivery of biologically-active compounds, particularly psychotropic, neurotropic and neurological drugs and agents, to physiologically restricted or protected sites. Advantageous embodiments of such delivery means are formulated to efficiently deliver the biologically-active compound to a physiologically-protected site, such as the brain or central nervous system, while minimizing hepatic and renal uptake of the agent or hematopoietic insult resulting therefrom.

SUMMARY OF THE INVENTION

The present invention is directed to an improved method for delivering biologically-active compounds, particularly drugs including preferably psychotropic, neurotropic and neurologically-acting drugs, to physiologically protected sites in an animal in vivo. This delivery system achieves specific delivery of such biologically-active compounds through conjugating the compounds with a polar lipid carrier. This invention has the specific advantage of facilitating the entry of such compounds into cells and tissues protected by such physiological barriers as the blood-brain barrier via a polar lipid carrier, achieving effective intracellular concentration of such compounds more efficiently and with more specificity than conventional delivery systems.

The invention provides compositions of matter comprising a biologically-active compound covalently linked to a polar lipid carrier molecule. Preferred embodiments also comprise a spacer molecule having two linker functional groups, wherein the spacer has a first end and a second end and wherein the lipid is attached to the first end of the spacer through a first linker functional group and the biologically-active compound is attached to the second end of the spacer through a second linker functional group. In preferred embodiments, the biologically-active compound is a drug, most preferably a psychotropic, neurotropic or neurologically-acting drug or agent, or an antioxidant. Preferred polar lipids include but are not limited to acyl- and acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid. Preferred biologically-active compounds include neurotropic agents such as L-dopa, hydroxytryptamine and metabolites thereof; amantadine, benztropine, bromocryptine, diphenhydramine, levadopa (a particularly preferred embodiment) and combinations thereof (e.g., with carbidopa as provided as Sinemet®); pergolid, trihexphenidyl, ethosuximide, valproic acid, carbamazepine (e.g., Tegretol®) and, in a particularly preferred embodiment, the 10- or 11-hydroxy analogues of carbamazepine; primidone, gabapentin in a particularly preferred embodiment; lamotrigine in a particularly preferred embodiment; felbamate, paramethadione and trimethadione; phenothiazines, thioxanthemes and related compounds; clozapine, haldoperidol, loxapine (Loxitane®), benzodiazapene antidepressants of the norepinephrine reuptake inhibitor type; monoamine oxidase inhibitors, and antioxidants such as carotenes, glutathione and N-acetylcysteine. Pharmaceutical compositions comprising the drug/polar lipid conjugates of the invention are also provided.

The invention also provides compositions of matter comprising a biologically-active compound covalently linked to a lipid, most preferably a polar lipid, carrier molecule via a spacer molecule wherein the spacer allows the biologically-active compound to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of the biologically-active compound at an intracellular site. Other embodiments of the spacer facilitate the enzymatic release of the biologically-active compound at an intracellular site. In particularly preferred embodiments, the spacer functional group is hydrolyzed by an enzymatic activity found in brain tissue, including neuronal, glial and other brain cell types, preferably an esterase and most preferably an esterase having a differential expression and activity profile in the appropriate target cell type. In additional preferred embodiments, specific release of biologically-active compounds is achieved by enzymatic or chemical release of the biologically-active compound by extracellular cleavage of a cleavable linker moiety via an enzymatic activity specific for brain tissue, with resulting specific uptake of the released psychotropic, neurotropic or neurological agent by the appropriate cell in said tissue.

In another embodiment of this aspect of the invention, the spacer molecule is a peptide of formula (amino acid)$_n$, wherein n is an integer between 2 and 25, preferably wherein the peptide comprises a polymer of one or more amino acids.

In other embodiments of the compositions of matter of the invention, the biologically-active compound of the invention has a first functional linker group, and a lipid, most preferably a polar lipid, carrier has a second functional linker group, and the compound is covalently linked directly to the lipid carrier by a chemical bond between the first and second functional linker groups. In preferred embodiments, each of the first and second functional linker groups is a hydroxyl group, a primary or secondary amino group, a phosphate group or substituted derivatives thereof or a carboxylic acid group.

In another aspect of the invention is provided compositions of matter comprising a drug, most preferably an a psychotropic, neurotropic or neurological drug or agent, covalently linked to a polar lipid carrier molecule. Preferred embodiments also comprise a spacer molecule having two linker functional groups, wherein the spacer has a first end and a second end and wherein the lipid is attached to the first end of the spacer through a first linker functional group and the drug is attached to the second end of the spacer through a second linker functional group. Preferred embodiments of the invention are provided wherein the drug is a psychotropic, neurotropic or neurological drug or agent. Preferred polar lipids include but are not limited to acyl- and acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid. Preferred psychotropic, neurotropic or neurological drugs or agents comprising the conjugates of the invention include L-dopa, hydroxytryptamine and metabolites thereof; amantadine, benztropine, bromocryptine, diphenhydramine, levadopa (a particularly preferred embodiment) and combinations thereof (e.g., with carbidopa as provided as Sinemet®); pergolid, trihexphenidyl, ethosuximide, valproic acid, carbamazepine (e.g., Tegretol®) and, in a particularly preferred embodiment, the 10- or 11-hydroxy analogues of carbamazepine; primidone, gabapentin in a particularly preferred embodiment; lamotrigine in a particularly preferred embodiment; felbamate, paramethadione and trimethadione; phenothiazines, thioxanthemes and related compounds; clozapine, haldoperidol, loxapine (Loxitane®), benzodiazapene antidepressants of the norepinephrine reuptake inhibitor type; monoamine oxidase inhibitors, and antioxidants such as carotenes, glutathione and N-acetylcysteine. Pharmaceutical compositions comprising the drug/polar lipid conjugates of the invention are also provided.

The invention also provides compositions of matter comprising a psychotropic, neurotropic or neurological drug or agent, covalently linked to a polar lipid carrier molecule via a spacer molecule, wherein the spacer allows the drug to act without being released at an intracellular site. In these embodiments of the invention, the first linker functional group attached to the first end of the spacer is characterized as "strong" and the second linker functional group attached to the second end of the spacer is characterized as "weak", with reference to the propensity of the covalent bonds between each end of the spacer molecule to be broken.

In other embodiments of the compositions of matter of the invention, the spacer allows the facilitated hydrolytic release of a psychotropic, neurotropic or neurological drug or agent at an intracellular site. Other embodiments of the spacer facilitate the enzymatic release of the psychotropic, neurotropic or neurological drug or agent of the invention at an intracellular site. In particularly preferred embodiments, the spacer functional group is hydrolyzed by an enzymatic activity found in a physiologically-protected site, such as the brain and central nervous system and more particularly including neuronal, glial and other brain cell types, wherein said enzymatic activity is preferably an esterase and most preferably an esterase having a differential expression and activity profile in different tissue cell types. In additional preferred embodiments, specific release of the psychotropic, neurotropic or neurological drug or agent of the invention is achieved by enzymatic or chemical release of these drugs by extracellular cleavage of a cleavable linker moiety via an enzymatic activity specific for, for example, brain tissue, followed by specific uptake of the released psychotropic, neurotropic or neurological drug or agent by the appropriate cell in said tissue.

In another embodiment of this aspect of the invention, the spacer molecule is a peptide of formula (amino acid)$_n$, wherein n is an integer between 2 and 25, preferably wherein the peptide comprises a polymer of one or more amino acids.

In still further embodiments of the compositions of matter of the invention are provided psychotropic, neurotropic or neurological drugs or agents having a first functional linker group, and a polar lipid carrier having a second functional linker group, wherein the drug is covalently linked directly to the polar lipid carrier by a chemical bond between the first and second functional linker groups. In preferred embodiments, each of the first and second functional linker groups is a hydroxyl group, a primary or secondary amino group, a phosphate group or substituted derivatives thereof or a carboxylic acid group. Preferred psychotropic, neurotropic or neurological drugs or agents comprising the conjugates of the invention include L-dopa, hydroxytryptamine and metabolites thereof; amantadine, benztropine, bromocryptine, diphenhydramine, levadopa (a particularly preferred embodiment) and combinations thereof (e.g., with carbidopa as provided as Sinemet®); pergolid, trihexphenidyl, ethosuximide, valproic acid, carbamazepine (e.g., Tegretol®) and, in a particularly preferred embodiment, the 10- or 11-hydroxy analogues of carbamazepine; primidone, gabapentin in a particularly preferred embodiment; lamotrigine in a particularly preferred embodiment; felbamate, paramethadione and trimethadione; phenothiazines, thioxanthemes and related compounds; clozapine, haloperidol, loxapine (Loxitane®), benzodiazapene antidepressants of the norepinephrine reuptake inhibitor type; monoamine oxidase inhibitors, and antioxidants such as carotenes, glutathione and N-acetylcysteine. Preferred polar lipids include but are not limited to acyl- and acylated carnitine, sphingosine, ceramide, phosphatidyl choline, phosphatidyl glycerol, phosphatidyl ethanolarnine, phosphatidyl inositol, phosphatidyl serine, cardiolipin and phosphatidic acid. Pharmaceutical compositions comprising the drug/polar lipid conjugates of the invention are also provided.

Preferred embodiments of this aspect of the invention include compositions of matter that are polar lipid conjugates of anticonvulsive agents, antiparkinsonian drugs, alkaloids, catecholamines including dopamine analogues and derivatives, muscarinic receptor agonists and antagonists, cholinergic receptor agonists and antagonists, calcium channel blockers, γ-aminobutyric acid (GABA) receptor agonists, antagonists, and uptake inhibitors and enhancers; phenothiazines, thioxanthemes and related compounds; clozapine, haloperidol, loxapine (Loxitane®), benzodiazapene antidepressants of the norepinephrine reuptake inhibitor type; monoamine oxidase inhibitors; antidepressants and antimanic agents, antioxidants and other compounds that mitigate the effects of reactive oxygen species (for the treatment of Alzheimer's disease, Parkinson's disease, or other neurodegenerative conditions such as ataxia telangiectasia and amyelolaterosclerosis (ALS)).

As disclosed herein, the invention comprehends a polar lipid-drug conjugate wherein the polar lipid selectively promotes association with and transit across certain physiological barriers to protected tissue sites, thereby facilitating delivery of drugs and other pharmaceutical agents to such physiologically restricted or protected sites. In embodiments comprising a spacer moiety, the spacer component of the conjugates of the invention will preferably act to specifically release the drug from the lipid at the target site; prevent the non-specific release from the drug from the lipid in the systemic circulation or in hepatic, renal or other inappropriate cells, tissue or organs; target the conjugate to a specific cell or cell type within the protected tissue; prevent interaction and/or uptake of the drug by hematopoietic, ocular, hepatic or renal tissues; or perform other functions to maximize the effectiveness of the drug.

This type of conjugate has numerous advantages. The drug-lipid conjugates of the invention provide delivery of a variety of psychotropic, neurotropic and neurological drugs and agents to physiologically restricted or protected sites in vivo at concentrations and pharmicokinetic rates not heretofore attainable. A benefit of this advantage is the achievement of therapeutic indices of agents in such protected sites whereby the agent is useful for achieving a desired therapeutic goal. Another benefit is decreased hepatic toxicity, hematopoietic suppression (such as thrombocytopenia, leukopenia, aplastic anemia, leukocytosis, eosinophilia, pancytopenia, agranulocytosis), reduced systemic metabolism, degradation and toxicity, reduced hepatic clearance, reduced systemic adverse drug interactions, and generally reduced side effects due to the achievement of a lower, therapeutically-effective dose as the result of surmounting the physiological barrier. These biological effects can also result in simplified dosage schedules, particularly for drugs with short systemic half-lives.

In addition, the lipid/drug conjugates promote the intracellular entry of a variety of potentially useful drugs at pharmokinetic rates not currently attainable. The range of targeted cell types is not limited per se by particular, limited biological properties of the cell (such as the number and type of specific receptor molecules expressed on the cell surface). In contrast to traditional attempts to simply target drugs to specific cells, the conjugates of the invention can also target drugs to specific intracellular organelles and other intracellular compartments. In certain preferred embodiment, the conjugates of the invention incorporate a variable spacer region that may allow pharmacologically-relevant rates of drug release from polar lipid carrier molecules to be engineered into the compositions of the invention, thereby increasing their clinical efficacy and usefulness. Thus, time-dependent drug release and specific drug release in cells expressing the appropriate degradative enzymes are a unique possibility using the drug-lipid conjugates of the invention.

In particular, felicitous design of the psychotropic, neurotropic/neurological drug/spacer/polar lipid conjugate can provide an in vivo reservoir of time-dependent drug release in the physiologically protected tissue, resulting in specific delivery of therapeutic amounts to such tissues using a reduced dosage regime to minimize non-specific, systemic and deleterious side effects. In such formulations, the amount and activity of the psychotropic, neurotropic or neurological drug can be modulated by release via cleavage, preferably hydrolytic cleavage, of the spacer moiety, most preferably by an enzymatic activity in the protected tissue (e.g., brain) that has a differential pattern of expression or activity in different cell types in said tissue. The conjugates of the invention can also be combined with other drug delivery approaches to further increase specificity and to take advantage of useful advances in the art.

Specific preferred embodiments of the present invention will become evident from the following more detailed description of certain preferred embodiments and the claims.

DETAILED DESCRIPTION OF THE PREFERRED EMBODIMENTS

Figure 1:
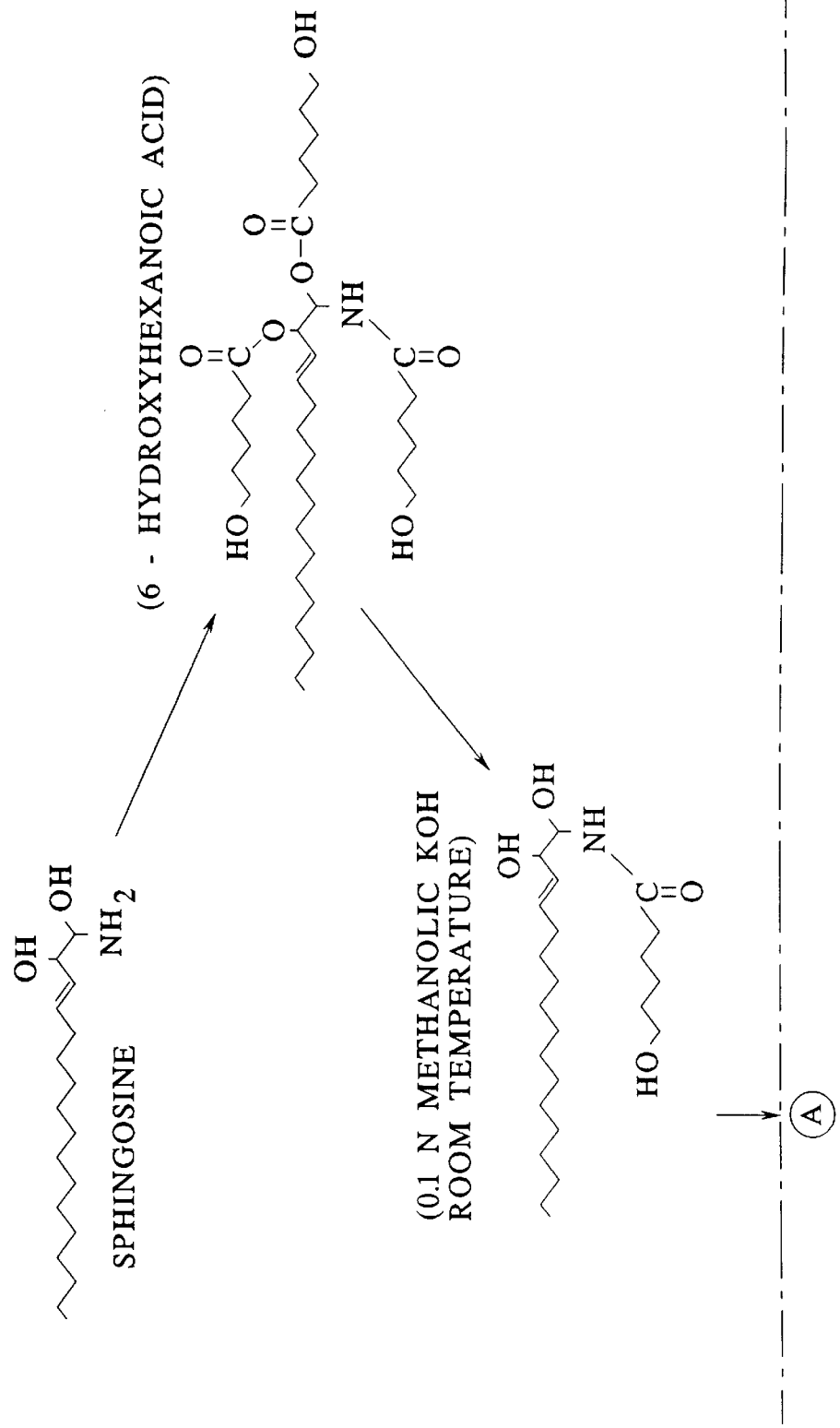
FIG. 1 depicts the synthetic scheme put forth in Example 1.
Figure 1:
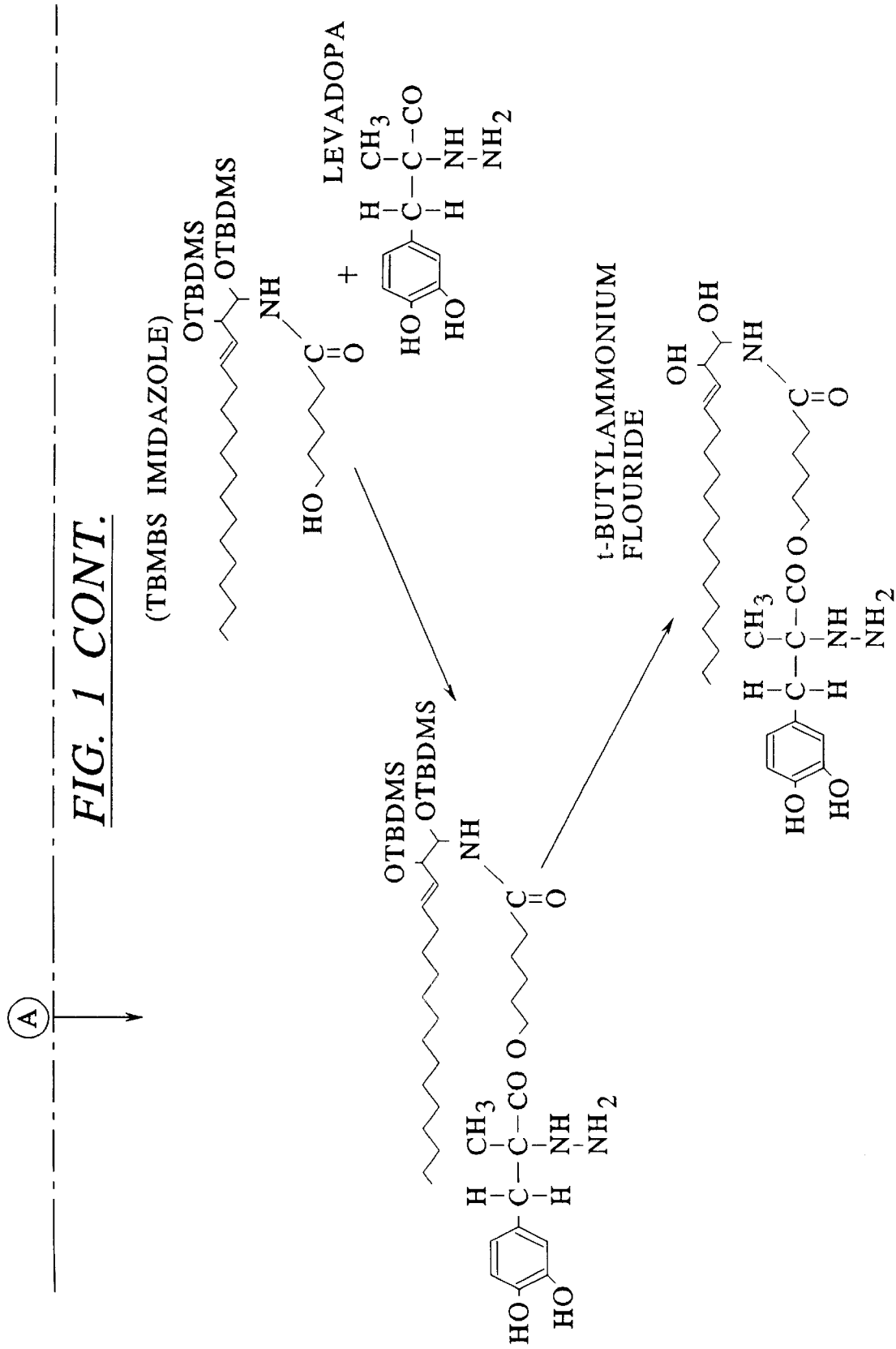

The present invention provides compositions of matter and methods for facilitating the entry into cells of biologically-active compounds. For the purposes of this invention, the term "biologically-active compound" is intended to encompass all naturally-occurring or synthetic compounds capable of eliciting a biological response or having an effect, either beneficial or cytotoxic, on biological systems, particularly cells and cellular organelles. These compounds are intended to include but are not limited to all varieties of drugs, particularly psychotropic, neurotropic and neurologically-acting drugs and agents.

As used herein the terms psychotropic, neurotropic and neurologically-acting drugs and agents are intended to include any drug, agent or compound having a neurological, neurotropic, or psychotropic effect in an animal, preferably a human. These terms are intended to encompass anti-inflammatory agents, corticosteroids, sedatives, tranquilizers, narcotics, analgesics, anesthetics, anticonvulsive and antispasmodic agents, antiparkinsonian drugs, alkaloids, catecholamines, including dopamine analogues and derivatives, muscarinic receptor agonists and antagonists, cholinergic receptor agonists and antagonists, calcium channel blockers, γ-aminobutyric acid (GABA) receptor agonists, antagonists, and uptake inhibitors and enhancers; phenothiazines, thioxanthemes and related compounds; clozapine, haldoperidol, loxapine (Loxitane®), benzodiazapene antidepressants of the norepinephrine reuptake inhibitor type; monoamine oxidase inhibitors; antidepressants and antimanic agents, antioxidants such as carotenes, glutathione, N-acetylcysteine or other molecules that mitigate the effects of reactive oxygen species for the treatment of Alzheimer's disease, Parkinson's disease, or other neurodegenerative conditions such as ataxia telangiectasia and amyelolaterosclerosis (ALS); neuroregenerative agents; and agents for the treatment of ischemia and other vascular diseases of the central nervous system. Appropriate formulations and pharmaceutical compositions of the neurotropic/neurological/psychotropic drug/polar lipid conjugates of the invention will be apparent and within the skill of one of ordinary skill in this art to advantageously prepare in view of the instant disclosure.

The compositions of matter provided by the invention comprise the biologically-active compounds of the invention covalently linked to a polar lipid carrier. A polar lipid carrier, as defined herein is intended to mean any polar lipid having an affinity for, or capable of crossing, a biological membrane and in particular a physiological barrier protecting certain cells, tissues and organs, including but not limited to sphingosine, ceramide, phosphatidyl choline, phosphatidyl glycerol, phosphatidyl ethanolarnine, phosphatidyl inositol, phosphatidyl serine, cardiolipin, phosphatidic acid, sphingomyelin and other sphingolipids, as these terms are understood in the art (see, Lehninger, *Biochemistry*, 2d ed., Chapters 11 & 24, Worth Publishers: New York, 1975). Additionally, certain other lipids, such as acylated carnitine, comprise the conjugates of the invention (see Small, 1986, "From alkanes to phospholipids," *Handbook of Lipid Research: Physical Chemistry of Lipids*, Volume 4, Chapters 4 and 12, Plenum Press: New York). For the purposes of this invention, the term "polar lipid" is not intended to encompass "lipoid"-type compounds, such as, for example, aliphatic phosphonates (see, for example, U.S. Pat. No. 5,413,996).

The compositions of matter of the invention may be further comprised of a spacer moiety comprising a first end and a second end, each end of the spacer having a functional linking group. For the purposes of this invention, the term "spacer" or "spacer moiety" is intended to encompass any chemical entity that links the biologically-active compound and the polar lipid. Such spacer moieties may be designed to facilitate the attachment of the conjugates of the invention to a target cell, or to facilitate, influence, modulate or regulate the release of the biologically-active compound at the desired target site. Such spacers may also facilitate enzymatic release at certain intracellular sites. Spacer groups, as described herein, include, but are not limited to aminohexanoic acid, polyglycine, polyamides, polyethylenes, and short functionalized polymers having a carbon backbone which is from one to about twelve carbon molecules in length. Particularly preferred embodiments of such spacer moieties comprise peptides of formula (amino acid)$_n$, wherein n is an integer between 2 and 25 and the peptide is a polymer of one or more amino acids.

The term "linker functional group" is defined herein as any functional group for covalently binding the polar lipid carrier or biologically-active agent to the spacer group. These groups can be designated either "weak" or "strong" based on the stability of the covalent bond which the linker functional group will form between the spacer and either the polar lipid carrier or the biologically-active compound. The weak functionalities include, but are not limited to phosphoramide, phosphoester, carbonate, amide, carboxylphosphoryl anhydride, thioester and most preferably ester. The strong functionalities include, but are not limited to ether, thioether, amine, amide and most preferably ester. The use of a strong linker functional group between the spacer group and the biologically-active compound will tend to decrease the rate at which the compound will be released at the target site, whereas the use of a weak linker functional group between the spacer group and the compound may act to facilitate release of the compound at the target site. Enzymatic release is, of course, also possible, but such enzyme-mediated modes of release will not necessarily be correlated with bond strength in such embodiments of the invention. Spacer moieties comprising enzyme active site recognition groups, such as spacer groups comprising peptides having proteolytic cleavage sites therein, are envisioned as being within the scope of the present invention.

Specifically, such specifically-cleavable peptides are preferably prepared so as to be recognized by enzymes present in brain and other physiologically restricted or protected sites in vivo, so that the drug is preferentially liberated from the polar lipid conjugate at appropriate drug delivery sites. An illustrative example of such a specifically-cleavable peptide is a portion of the proopiomelanocortin family of peptides, which are cleaved in mammalian brain tissue to release a variety of peptides hormones and effector molecules, such as the enkephalins. Other beneficial and advantageous specifically-cleavable peptides will be recognized by those of ordinary skill in the art.

The drug/polar lipid conjugates of the invention are preferably provided comprised of spacer moieties that impart differential release properties on the conjugates related to differential expression or activity of enzymatic activities in physiologically restricted or protected sites in comparison with such activities in systemic circulation or in inappropriate targets, such as hepatic, renal or hematopoietic tissues. Differential release is also provided in certain embodiments in specific cell types comprising such physiologically protected tissues.

In particularly preferred embodiments of the present invention are provided psychotropic/neurotropic/neurological drug/polar lipid conjugates for specific delivery to brain tissue for the alleviation or amelioration of pathological disease states in the brain. Thus, the present invention provides methods and compositions of matter for facilitating the transit of such polar lipid conjugates of psychotropic, neurotropic or neurological drugs, agents and compounds across the blood-brain barrier and into targeted regions of the brain, for the treatment of animal, preferably human, diseases and pathological conditions. Among the most common such diseases and conditions are Alzheimer's disease, Parkinson's disease, epilepsy and other seizure disorders (such as petit mal, grand mal, tonic-clonic seizure disorder, parietal complex seizure, and psychomotor seizures), migraine, neurodegenerative conditions such as ataxia telangiectasia and ALS, Lennox-Gastaut syndrome, neuropathy such as trigeminal neuralgia, diabetic neuropathy, shingles, and psychological disorders, including bipolar disorder, explosive aggression, depression and agitation associated with elderly dementia.

The invention provides polar lipid/drug conjugates comprising psychotropic, neurotropic and neurological drugs, agents and compounds including but not limited to L-dopa, hydroxytryptamine and metabolites thereof, amantadine, benztropine, bromocriptine, diphenhydramine, levadopa (a particularly preferred embodiment) and combinations thereof (e.g., with carbidopa as provided as Sinemet®); pergolid, trihexphenidyl, ethosuximide, valproic acid, carbamazepine (e.g., Tegretol®) and, in a particularly preferred embodiment, the 10- or 11-hydroxy analogues of carbamazepine; primidone, gabapentin in a particularly preferred embodiment; lamotrigine in a particularly preferred embodiment; felbamate, paramethadione and trimethadione; phenothiazines, thioxanthemes and related compounds; clozapine, haldoperidol, loxapine (Loxitane®), benzodiazapene antidepressants of the norepinephrine reuptake inhibitor type; monoamine oxidase inhibitors, and antioxidants such as carotenes, glutathione and N-acetylcysteine.

The invention specifically provides methods for preparing and administering such psychotropic, neurotropic and neurological drugs, agent and compounds for use in treating pathological conditions in vivo.

Animals to be treated with the drug-polar lipid conjugates using the methods of the invention are intended to include all vertebrate animals, preferably domesticated animals, such as cattle, horses, goats, sheep, fowl, fish, household pets, and others, as well as wild animals, and most preferably humans.

The following Examples illustrate certain aspects of the above-described method and advantageous results. The following examples are shown by way of illustration and not by way of limitation.

EXAMPLE 1

A polar lipid conjugate with levadopa is prepared by conjugating a linker moiety to a polar lipid via an amide linkage, as follows. A polar lipid (sphingosine) comprising unconjugated amino groups is reacted with a 6-hydroxyhexanoic acid (6-HHA) in the presence of 1.0 equivalent of dicyclohexyl carbodiimide (DCCD) overnight at 40–50° C. The derivatized sphingosine was then reacted with 0.1N methanolic potassium hydroxide at room temperature, and then treated with 2.0 equivalents of tert-butyl dimethyl silyl imidazole (TBDMS) overnight at 40–50° C. This sphingosine species, derivatized by an amide linkage between the amino group of sphingosine and the carboxylate group of 6-HHA, is then esterified at the unprotected 6-HHA derived hydroxyl group with bis-TBDMS-levadopa and DCCD overnight at 40–50° C. The levadopa-sphingosine conjugate is then deprotected by treatment with 4.–0 equivalents of t-butylammonium fluoride at 0° C. for 10 minutes. This reaction scheme is illustrated in FIG. 1. Synthesis of conjugates comprising ester linkages as described in Examples 1, 2 and 3, and of amine linkages as described in Examples 4 and 5 advantageously permits control of rates of drug release based on differences in amount and rates of amidase or esterase enzymatic activity in the brain, wherein amidase-sensitive linkages generally provide a longer time release course than esterase-sensitive linkages.

EXAMPLE 2

Figure 2:
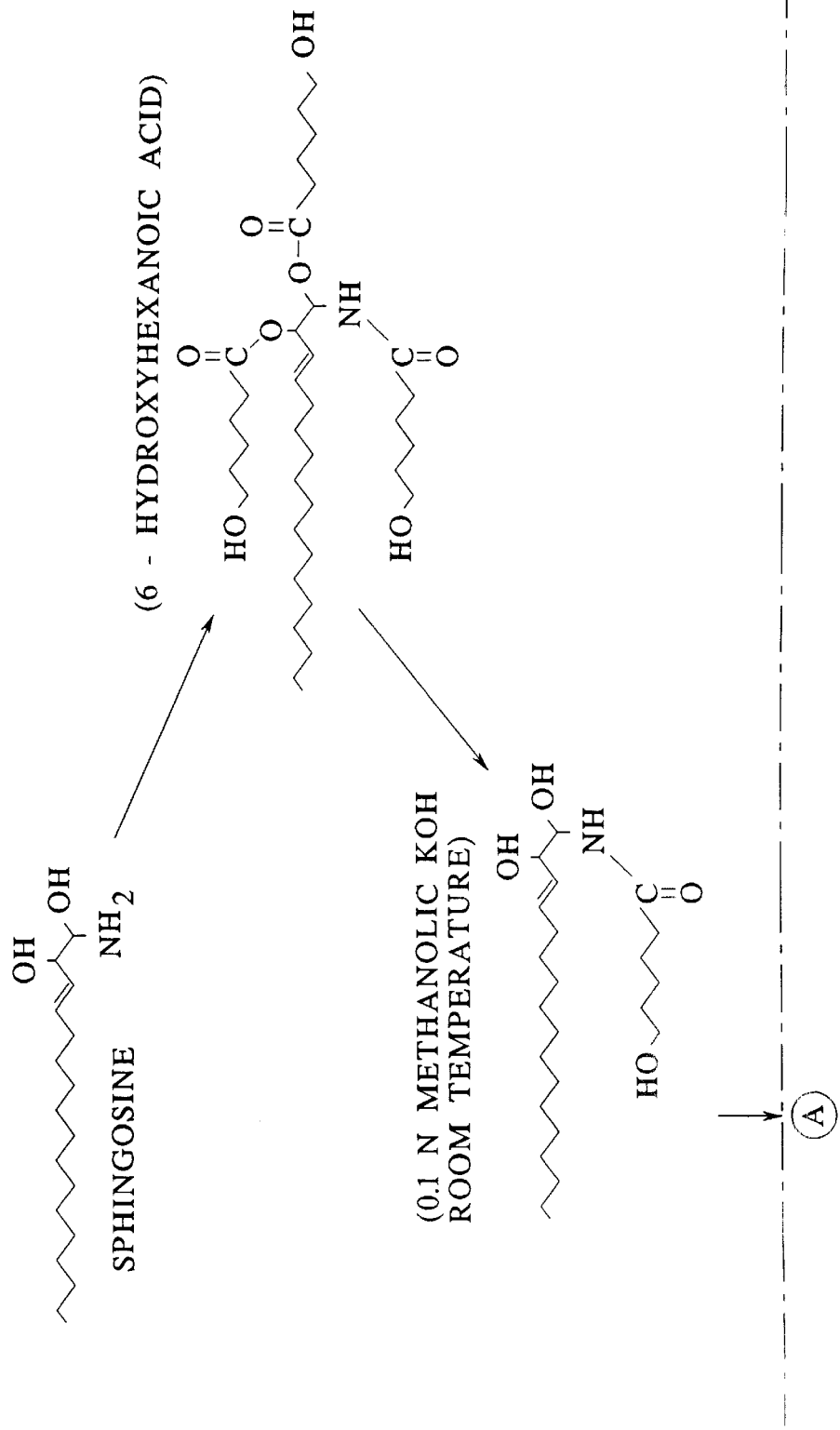
FIG. 2 depicts the synthetic scheme put forth in Example 2.
Figure 2:
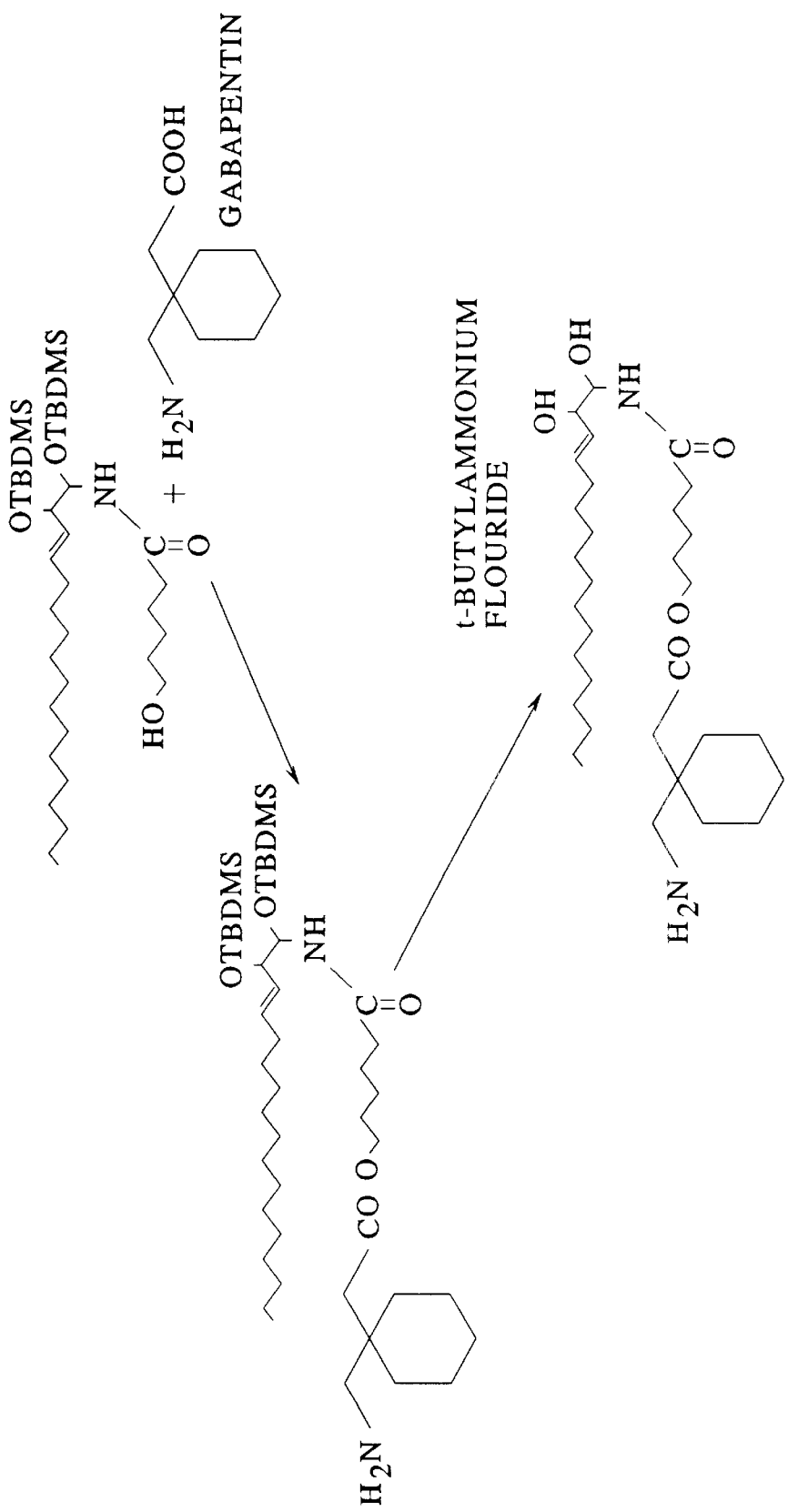

A polar lipid conjugate with gabapentin comprising an ester linkage is prepared by conjugating a linker moiety to a polar lipid via an amide linkage, as follows. A polar lipid (sphingosine) comprising unconjugated amino groups is reacted with a 6-hydroxyhexanoic acid (6-HHA) in the presence of 1.0 equivalent of dicyclohexyl carbodiimide (DCCD) overnight at 40–50° C. The derivatized sphingosine was then reacted with 0.1N methanolic potassium hydroxide at room temperature, and then treated with 2.0 equivalents of tert-butyl dimethyl silyl imidazole (TBDMS) overnight at 40–50° C. This sphingosine species, derivatized by an amide linkage between the amino group of sphingosine and the carboxylate group of 6-HHA, is then esterified at the unprotected 6-HHA derived hydroxyl group with gabapentin and DCCD overnight at 40–50° C. The gabapentin-sphingosine conjugate is then deprotected by treatment with with 4.–0 equivalents of t-butylammonium fluoride at 0° C. for 10 minutes. This reaction scheme is illustrated in FIG. 2.

EXAMPLE 3

Figure 3:
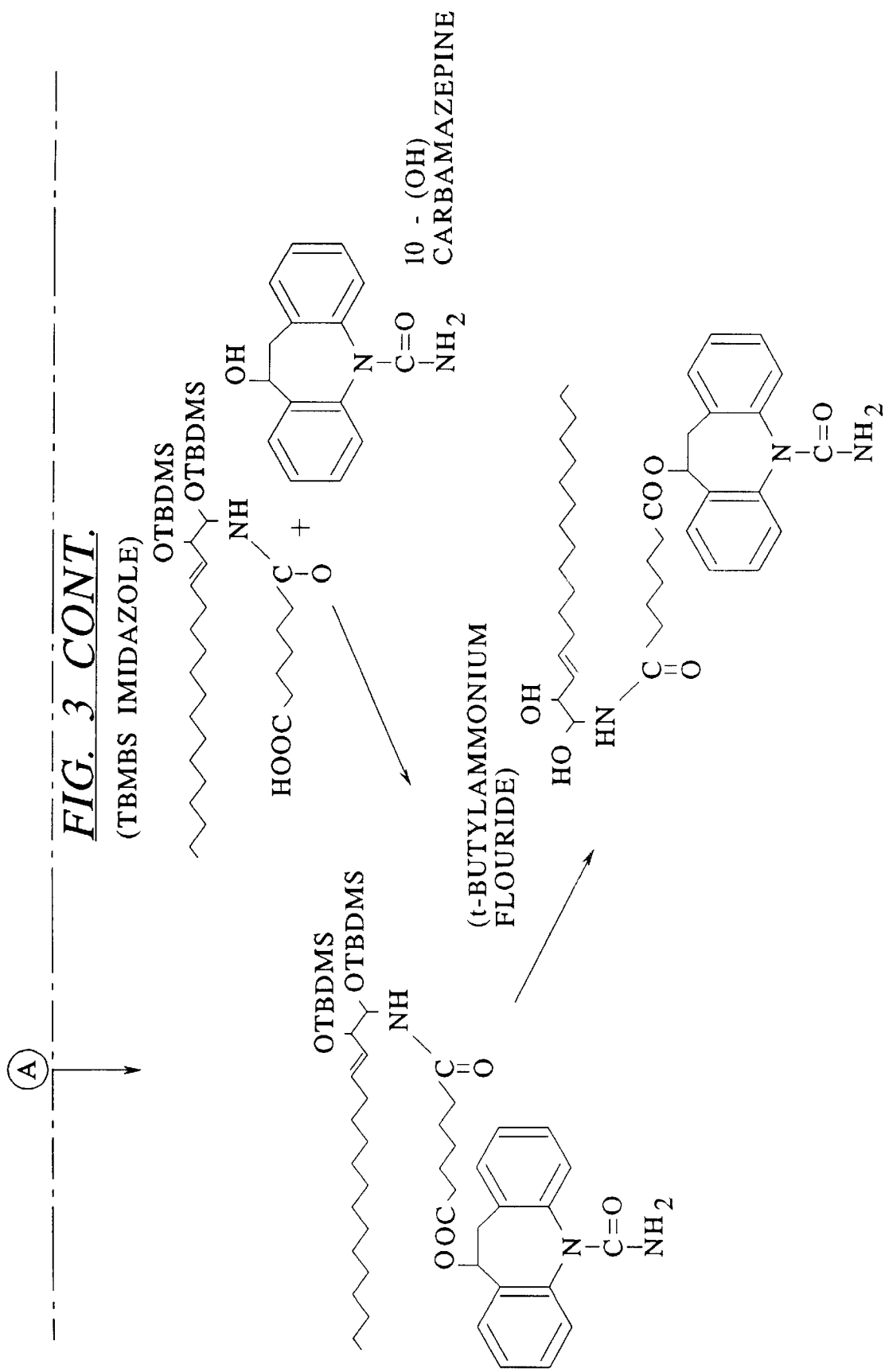
FIG. 3 depicts the synthetic scheme put forth in Example 3.

A polar lipid conjugate with 10-hydroxycarbamazepine comprising an ester linkage is prepared by conjugating a linker moiety to a polar lipid via an amide linkage, as follows. A polar lipid (sphingosine) comprising unconjugated amino groups is reacted with a 6-hydroxyhexanoic acid (6-HHA) in the presence of 1.0 equivalent of dicyclohexyl carbodiimide (DCCD) overnight at 40–50° C. The derivatized sphingosine was then reacted with 0.1N methanolic potassium hydroxide at room temperature, and then treated with 2.0 equivalents of tert-butyl dimethyl silyl imidazole (TBDMS) overnight at 40–50° C. This sphingosine species, derivatized by an amide linkage between the amino group of sphingosine and the carboxylate group of 6-HHA, is then esterified at the unprotected 6-HHA derived hydroxyl group with with 10-hydroxycarbamazepine and DCCD overnight at 40–50° C. The 10-hydroxycarbamazepine-sphingosine conjugate is then deprotected by treatment with with 4.-0 equivalents of t-butylammonium fluoride at 0° C. for 10 minutes. This reaction scheme is illustrated in FIG. 3.

EXAMPLE 4

Figure 4:
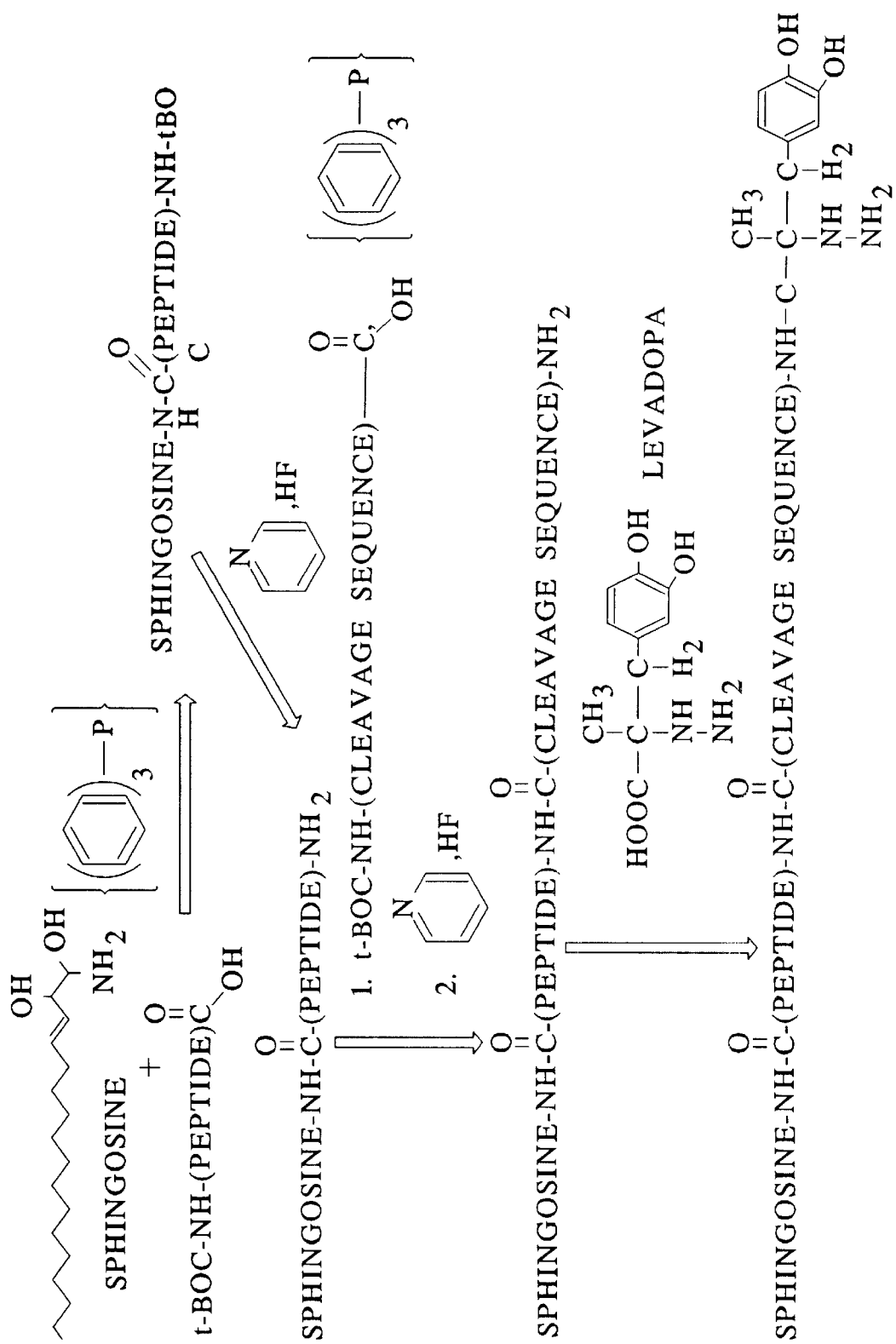
FIG. 4 depicts the synthetic scheme put forth in Example 4.

A polar lipid conjugate of gabapentin, hydroxycarbamazepine or levadopa is prepared by conjugating a specifically-cleavable peptide as a linker between a polar lipid and a drug as follows. An derivatized polar lipid comprising unconjugated amino groups is reacted with a proteolytically-inert peptide in which the terminal amine and any of the constituent amino acid sidechain reactive amines are covered by tert-butoxycarbonyl (t-Boc) protecting groups in the presence of triphenyl phosphine as described by Kishimoto (1975, *Chem. Phys. Lipids* 15: 33–36). The peptide/polar lipid conjugate is then reacted in the presence of pyridine hydrofluoride as described by Matsuura et al. (1976, *J. Chem. Soc. Chem. Comm.* xx: 451–459) to remove the t-Boc protecting groups. The peptide/polar lipid is then conjugated to the specifically-cleavable peptide, in which the terminal amine and any of the constituent amino acid sidechain reactive amines are covered by t-Boc protecting groups, as described in the presence of triphenyl phosphine. After deprotection of reactive amines with pyridine hydrofluoride as described, gabapentin, hydroxycarbamazepine or levadopa is conjugated to a free amino group of the polar lipid/peptide/specifically-cleavable peptide via a reactive carboxylic acid group to yield a drug/polar lipid conjugate of the invention. This reaction scheme is illustrated in FIG. 4 for sphingosine conjugated to levadopa.

EXAMPLE 5

Figure 5:
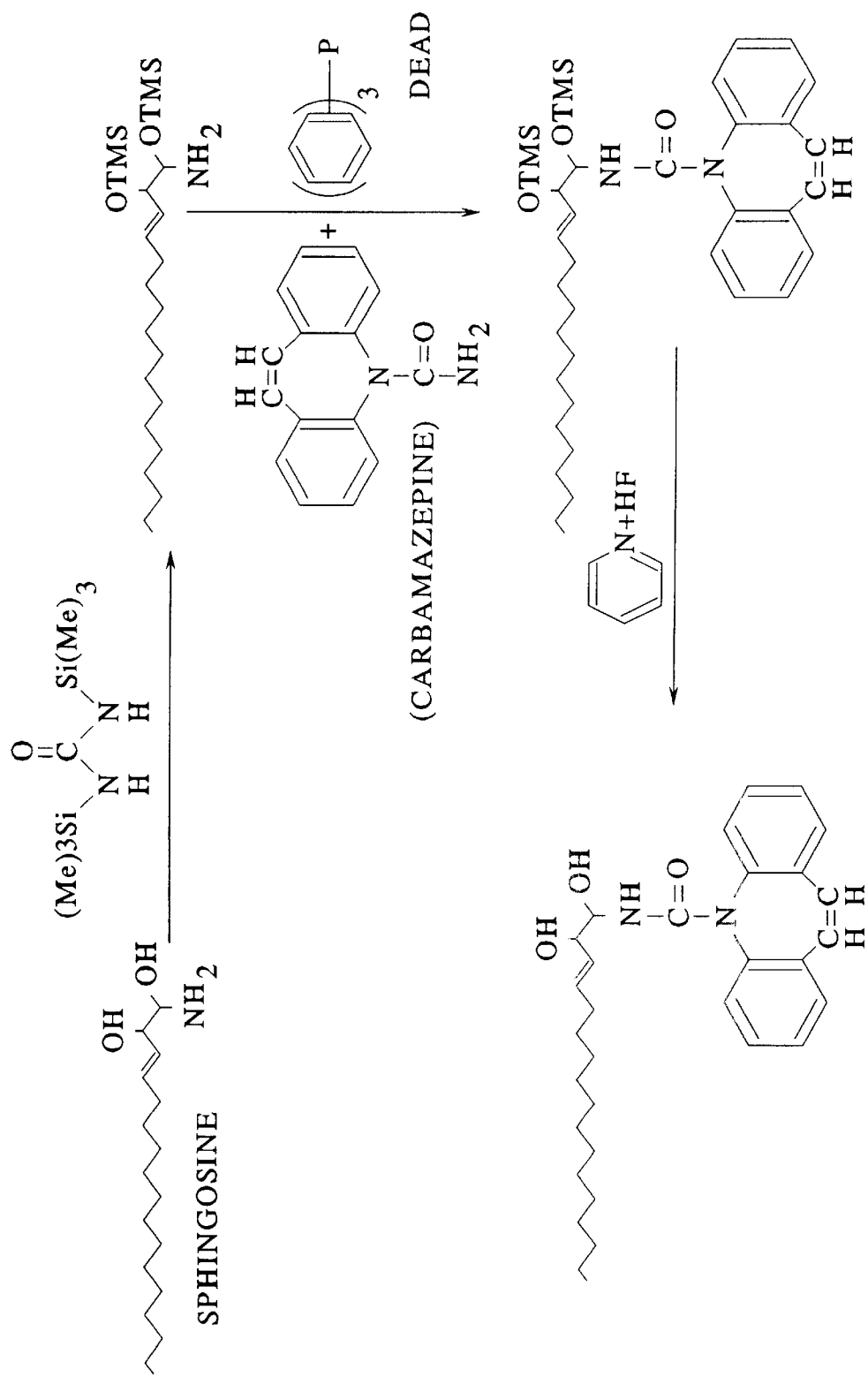
FIG. 5 depicts the synthetic scheme put forth in Example 5.

Carbamazepine is directly conjugated to sphingosine via an amide linkage as follows. Sphingosine is reacted with 1,3 bis(trimethylsilyl)urea as described by Verbloom et al. (1981, *Synthesis* 1032: 807–809) to give a trimethylsilyl derivative of sphingosine. The sphingosine derivative is then conjugated with carbamazepine in the presence of triphenylphosphine as described by Kishimoto (Ibid.). The sphingosine-carbamazepine conjugate is then reacted in the presence of pyridine hydrofluoride as described by Matsuura et al. (Ibid.) to remove the t-Boc protecting group, to yield the drug/sphingosine conjugate covalently linked through an amide bond. This reaction scheme is illustrated in FIG. 5.

EXAMPLE 6

Figure 6A:
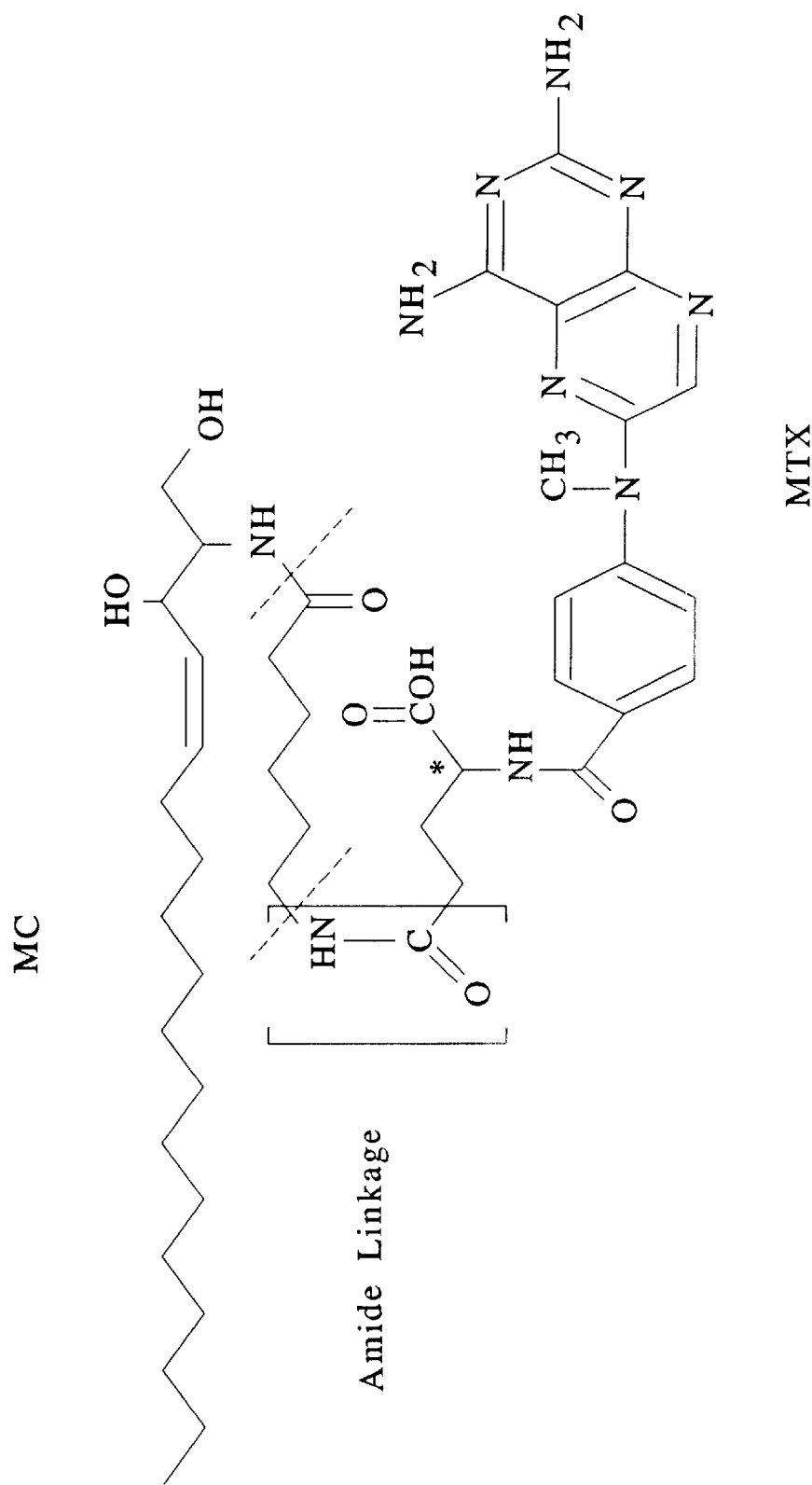
FIGS. 6A through 6D depict prodrugs tested as in Example 6.
Figure 6B:
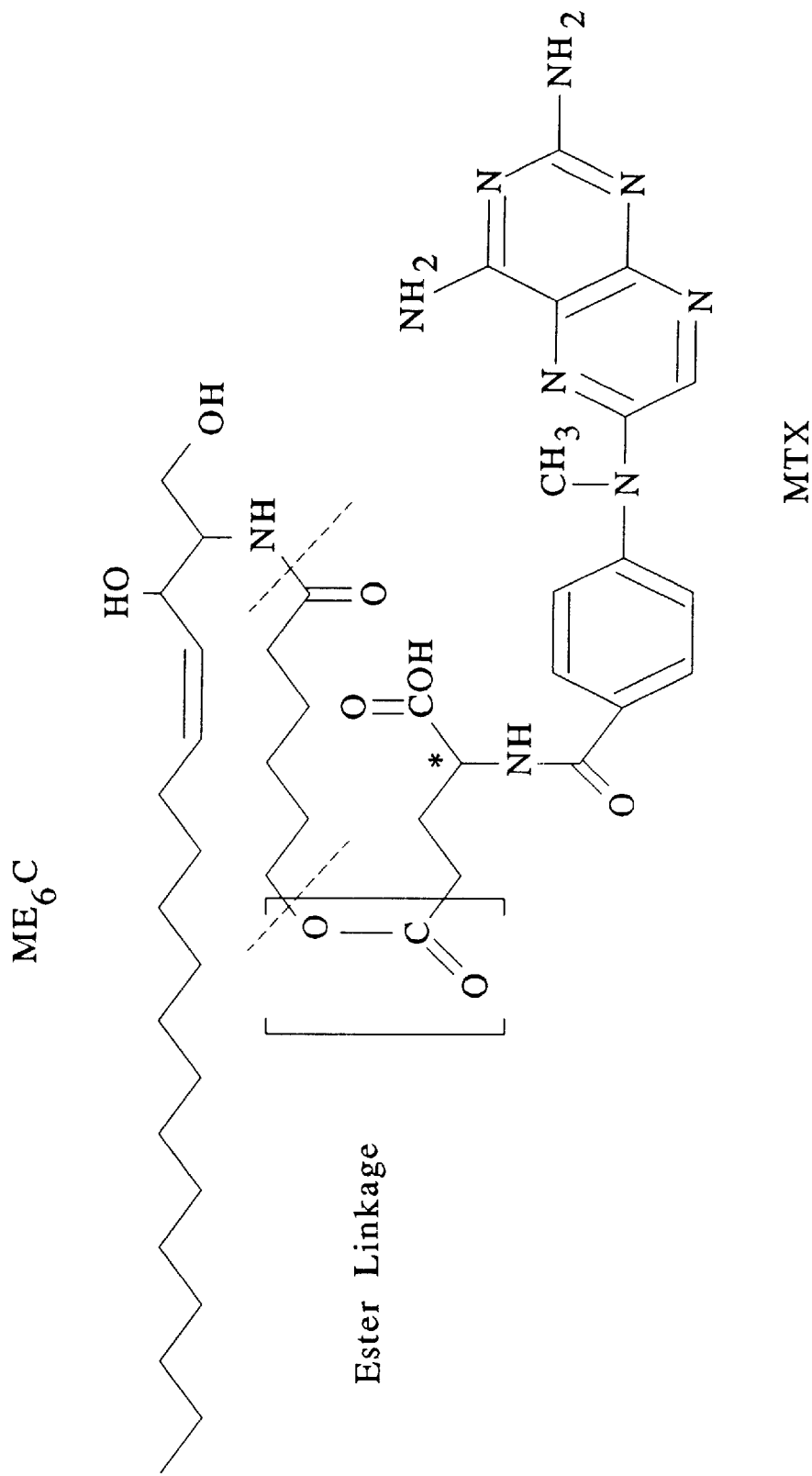
Figure 6C:
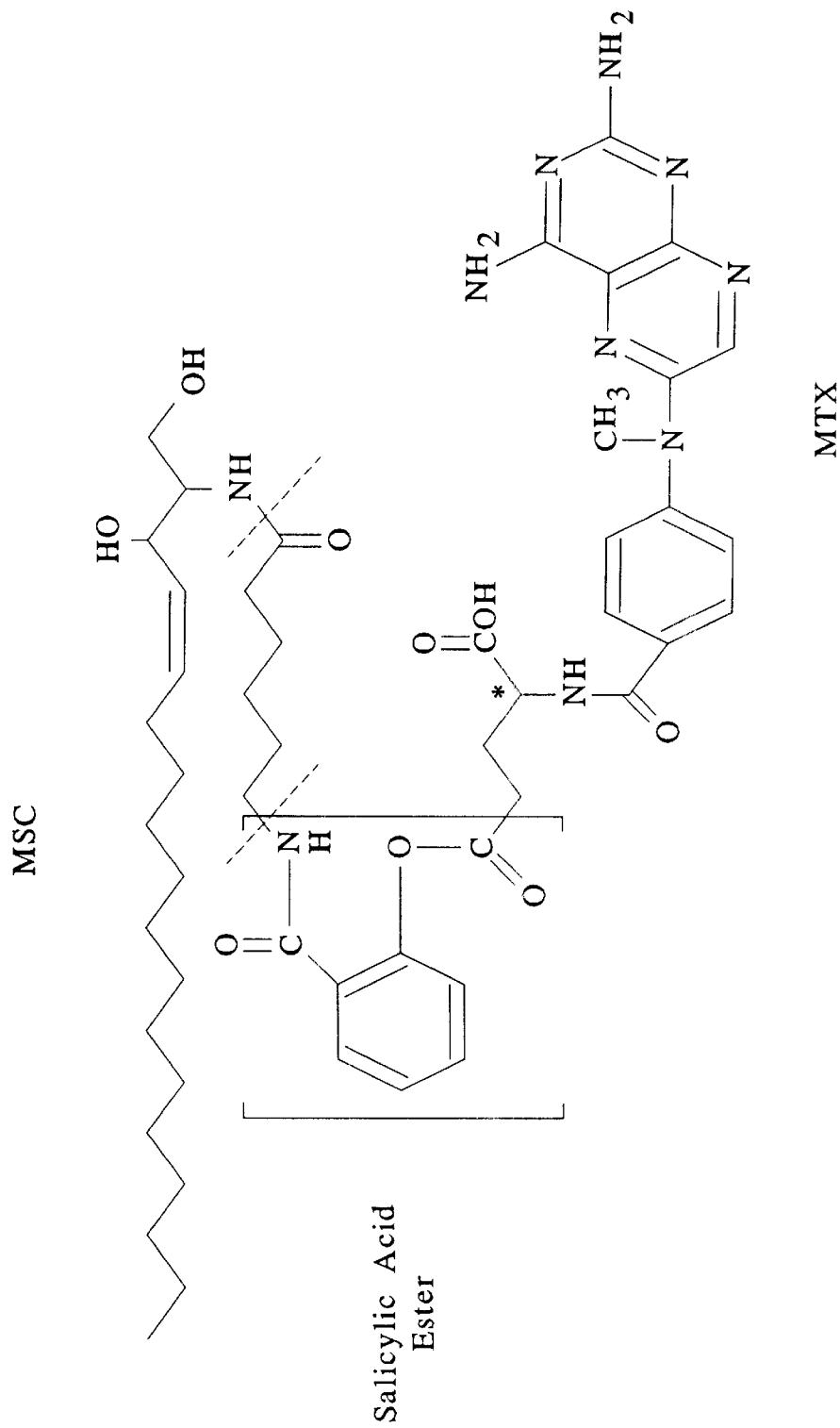
Figure 6D:
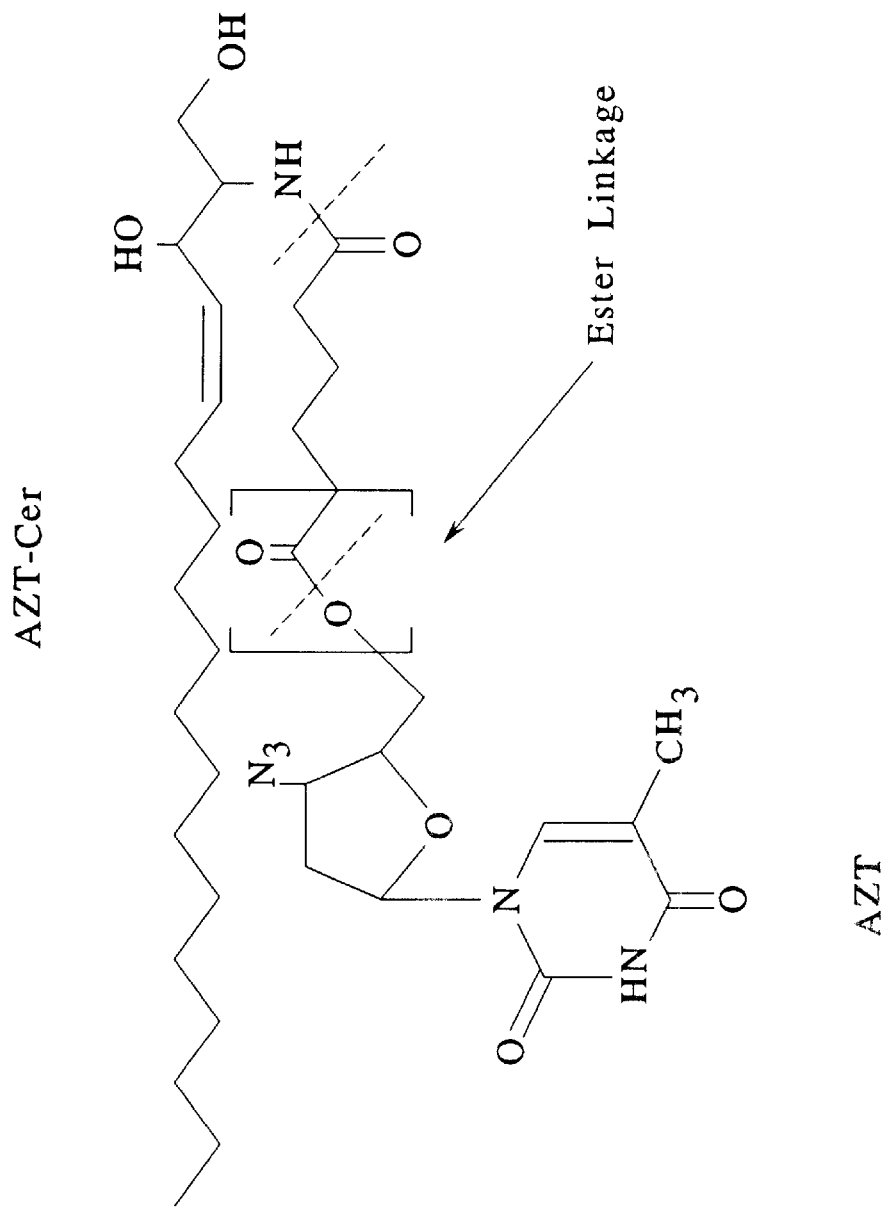

The effect of presenting a biologically active compound such as a drug to mammalian cells as a prodrug covalently linked to a polar lipid carrier moiety was determined as follows. The antifolate drug methotrexate was conjugated with a variety of polar lipid carriers via organic spacer moieties having specific reactive functional groups. A representative sample of such compounds is shown in FIGS. 6A through 6C, wherein MC represents Mtx linked to sphingosine via an amide bond to a 6-aminohexanoic acid spacer, $ME_6C$ represents Mtx linked to sphingosine via an ester linkage to a 6-hydroxyhexanoic acid spacer, and MSC represents Mtx linked to sphingosine via a salicylic acid ester linkage to a 6-aminohexanoic acid spacer. Also studied was a conjugate of azidothymidine linked to sphingosine via an ester linkage to a 6-hydroxyhexanoic acid spacer (N-AZT-ceramide; FIG. 6D). The compounds were tested for their growth inhibitory effects on murine NIH 3T3 cells growing in cell culture. About one million such cells per P100 tissue culture plate were grown in DMEM media supplemented with 10% fetal calf serum (GIBCO, Grand Island, N.Y.) in the presence or absence of a growth-inhibitory equivalent of each prodrug. Cell numbers were determined after 70 hours growth in the presence or absence of the prodrug. In a second set of experiments was included in the growth media an amount of a brain homogenate containing an enzymatically-active esterase.

The results from these experiments are shown in Table I. As can be seen from these data, the MC prodrug had no effect on the growth and survival of the cells. This result did not change upon co-incubation with the esterase-containing brain extract, which was expected due to the nature of the drug/spacer linkage (an amide bond). A different result was obtained with the $ME_6C$ conjugate. The prodrug was ineffective in inhibiting cell growth or survival in the absence of brain extract. Upon addition of the brain extract, a significant increase in Mtx cytotoxicity was observed. This is consistent with cleavage of the ester linkage by the brain extract-derived esterase. A similar result was obtained with the MCS conjugate, indicating that the brain extract esterase activity was capable of cleaving the salicylic acid ester.

Table II shows the results of drug uptake studies performed with the prodrug N-AZT-ceramide. Antiviral amounts of the prodrug conjugate were added to NIH 3T3 cell cultures, and the antiviral activity of the prodrug was found to be equivalent to the activity of free AZT. In addition, upon removal of the prodrug, intracellular retention of prodrug was found to be up to 15-fold higher than free AZT (Table II) over a 23 h period.

These results indicate that for Mtx-containing conjugates, the free drug must be released from the prodrug for biological activity. These results suggest that specific release of this drug, and perhaps others, can be achieved using cleavable linker moieties that are specifically cleaved only in pathogen-infected cells.

TABLE I

| Sample[1] | # cells/plate[2] | Sample[3] | # cells/plate[4] |
|---|---|---|---|
| Control/FBS | $7.8 \times 10^6$ | Control/FBS | $13 \times 10^6$ |
| $ME_6C$/FBS | $6.5 \times 10^6$ | MSC/FBS | $2.1 \times 10^6$ |
| $ME_6C$/brain | $2.7 \times 10^6$ | MSC/brain | $0.51 \times 10^6$ |
| Mtx/FBS | $0.16 \times 10^6$ | Mtx/FBS | $0.13 \times 10^6$ |
| Mtx/brain | $0.09 \times 10^6$ | Mtx/brain | $0.06 \times 10^6$ |
| Control/brain | N.D. | Control/brain | $6.2 \times 10^6$ |

[1] = cells incubated with drug/FBS or drug/brain extract for 1 hour at 37° C.
[2] = cell growth and survival determined 70 hours after drug addition
[3] = cells incubated with drug/FBS or drug/brain extract for 2 hours at 37° C.
[4] = cell growth and survival determined 72 hours after drug addition

TABLE II

| Time[1] | AZT[2] | N-AZT-Ceramide[2] |
|---|---|---|
| 0 hr. | 6.49 | 8.45 |
| 23 hr. | 0.55 | 7.78 |

[1] = time between the end of drug treatment and assay for intracellular drug concentration
[2] = $nM/10^6$ cells It should be understood that the foregoing disclosure emphasizes certain specific embodiments of the invention and that all modifications or alternatives equivalent thereto are within the spirit and scope of the invention as set forth in the appended claims.

What is claimed is:

1. A method for treating a pathological condition or disease state in cells, tissues or organs in an animal, the method comprising the step of administering to the animal a pharmaceutical composition comprising a psychotropic, neurotropic or neurological drug, a polar lipid carrier, two linker functional groups and a spacer, wherein the spacer has a first end and a second end and wherein the polar lipid is attached to the first end of the spacer through a first linker functional group and the drug is attached to the second end of the spacer through a second linker functional group, in an acceptable carrier or formulation and in an amount sufficient to alleviate the pathological condition or disease state in the animal.

2. A method for treating a pathological condition or disease state in skin of an animal, wherein the pathological condition or disease state results from an abnormal proliferation of cells in the animal, the method comprising the step of administering to the animal a pharmaceutical composition comprising a psychotropic, neurotropic or neurological drug, a polar lipid carrier, two linker functional groups and a spacer, wherein the spacer has a first end and a second end and wherein the polar lipid is attached to the first end of the spacer through a first linker functional group and the drug is attached to the second end of the spacer through a second linker functional group, in an acceptable carrier or formulation and in an amount sufficient to alleviate the pathological condition or disease state in the animal.

3. A method for treating a pathological condition or disease state in cells, tissues or organs in an animal, the method comprising administering to the animal a pharmaceutical composition comprising a psychotropic, neurotropic or neurological drug having a first functional linker group, and a polar lipid carrier having a second functional linker group, wherein the drug is covalently linked to the polar lipid carrier by a chemical bond between the first and second functional linker groups, in an acceptable carrier or formulation and in an amount sufficient to alleviate the pathological condition or disease state in the animal.

4. A method for treating a pathological condition or disease state in skin of an animal, wherein the pathological condition or disease state results from an abnormal proliferation of cells in the animal, the method comprising the step of administering to an animal a pharmaceutical composition comprising a psychotropic, neurotropic or neurological drug having a first functional linker group, and a polar lipid carrier having a second functional linker group, wherein the drug is covalently linked to the polar lipid carrier by a chemical bond between the first and second functional linker groups, in an acceptable carrier or formulation and in an amount sufficient to alleviate the pathological condition or disease state in the animal.

5. The method of claim 1 wherein the animal is a human.
6. The method of claim 2 wherein the animal is a human.
7. The method of claim 3 wherein the animal is a human.
8. The method of claim 4 wherein the animal is a human.
9. The method of claim 1, wherein the disease state is a neurological disease.
10. The method of claim 3, wherein the disease state is a neurological disease.
11. The method of claim 9, wherein the neurological disease is Parkinson's disease, epilepsy, seizure disorder, migraine or Lennox-Gastaut syndrome.
12. The method of claim 10, wherein the neurological disease is Parkinson's disease, epilepsy, seizure disorder, migraine or Lennox-Gastaut syndrome.
13. The method of claim 2, wherein the disease state is a neuropathy.
14. The method of claim 4, wherein the disease state is a neuropathy.
15. The method of claim 13, wherein the neuropathy is trigeminal neuralgia, diabetic neuropathy or shingles.
16. The method of claim 14, wherein the neuropathy is trigeminal neuralgia, diabetic neuropathy or shingles.
17. The method of claim 1, wherein the disease state is a psychological disorder.
18. The method of claim 3, wherein the disease state is a psychological disorder.
19. The method of claim 17, wherein the psychological disorder is bipolar disorder, explosive aggression, depression or agitation associated with elderly dementia.
20. The method of claim 18, wherein the psychological disorder is bipolar disorder, explosive aggression, depression or agitation associated with elderly dementia.
21. The method of claim 1 wherein the drug is L-dopa, hydroxytryptamine, amantadine, benztropine, bromocryptine, diphenhydramine, levadopa, pergolid, trihexphenidyl, ethosuximide, valproic acid, carbamazepine, 10-hydroxycarbamazepine, 11-hydroxycarbamazepine, primidone, gabapentin, lamotrigine, felbamate, paramethadione, trimethadione, phenothiazine, thioxantheme, clozapine, haldoperidol, loxapine, a benzodiazapene antidepressants of the norepinephrine reuptake inhibitor type, a monoamine oxidase inhibitor, carotene, glutathione or N-acetylcysteine.
22. The method of claim 2 wherein the drug is L-dopa, hydroxytryptamine, amantadine, benztropine, bromocryptine, diphenhydramine, levadopa, pergolid, trihexphenidyl, ethosuximide, valproic acid, carbamazepine, 10-hydroxycarbamazepine, 11-hydroxycarbamazepine, primidone, gabapentin, lamotrigine, felbamate, paramethadione, trimethadione, phenothiazine, thioxantheme, clozapine, haldoperidol, loxapine, a benzodiazapene antidepressants of the norepinephrine reuptake inhibitor type, a monoamine oxidase inhibitor, carotene, glutathione or N-acetylcysteine.
23. The method of claim 3 wherein the drug is L-dopa, hydroxytryptamine, amantadine, benztropine, bromocryptine, diphenhydramine, levadopa, pergolid, trihexphenidyl, ethosuximide, valproic acid, carbamazepine, 10-hydroxycarbamazepine, 11-hydroxycarbamazepine, primidone, gabapentin, lamotrigine, felbamate, paramethadione, trimethadione, phenothiazine, thioxantheme, clozapine, haldoperidol, loxapine, a benzodiazapene antidepressants of the norepinephrine reuptake inhibitor type, a monoamine oxidase inhibitor, carotene, glutathione or N-acetylcysteine.
24. The method of claim 4 wherein the drug is L-dopa, hydroxytryptamine, amantadine, benztropine, bromocryptine, diphenhydramine, levadopa, pergolid, trihexphenidyl, ethosuximide, valproic acid, carbamazepine, 10-hydroxycarbamazepine, 11-hydroxycarbamazepine, primidone, gabapentin, lamnotrigine, felbamate, paramethadione, trimethadione, phenothiazine, thioxantheme, clozapine, haldoperidol, loxapine, a benzodiazapene antidepressants of the norepinephrine reuptake inhibitor type, a monoamine oxidase inhibitor, carotene, glutathione or N-acetylcysteine.
25. The method of claim 1 wherein the polar lipid is acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin or phosphatidic acid.

26. The method of claim 2 wherein the polar lipid is acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin or phosphatidic acid.

27. The method of claim 3 wherein the polar lipid is acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin or phosphatidic acid.

28. The method of claim 4 wherein the polar lipid is acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin or phosphatidic acid.

* * * * *